(12) United States Patent
Chapman et al.

(10) Patent No.: US 9,205,157 B2
(45) Date of Patent: Dec. 8, 2015

(54) ANTI GANGLIOSIDE GD3 ANTIBODIES AND USES THEREOF

(75) Inventors: Paul Chapman, New York, NY (US); Lisa Davidson, Edingburgh (GB); José W. Saldanha, Middlesex (GB)

(73) Assignee: Sloan-Kettering Institute for Cancer Research, New York, NY (US)

( * ) Notice: Subject to any disclaimer, the term of this patent is extended or adjusted under 35 U.S.C. 154(b) by 480 days.

(21) Appl. No.: 13/530,761

(22) Filed: Jun. 22, 2012

(65) Prior Publication Data

US 2012/0276046 A1 Nov. 1, 2012

Related U.S. Application Data

(60) Division of application No. 12/541,958, filed on Aug. 16, 2008, now Pat. No. 8,207,308, which is a continuation-in-part of application No. PCT/US2008/054220, filed on Feb. 18, 2008.

(60) Provisional application No. 60/901,875, filed on Feb. 16, 2007.

(51) Int. Cl.
  *C07K 16/30* (2006.01)
  *A61K 51/10* (2006.01)
  *A61K 39/00* (2006.01)
  *A61K 39/395* (2006.01)

(52) U.S. Cl.
  CPC .............. *A61K 51/1066* (2013.01); *A61K 39/00* (2013.01); *A61K 39/39558* (2013.01); *C07K 16/3084* (2013.01); *C07K 2317/24* (2013.01); *C07K 2317/56* (2013.01); *C07K 2317/732* (2013.01); *C07K 2317/734* (2013.01); *C07K 2317/92* (2013.01)

(58) Field of Classification Search
  CPC ......................... A61K 39/00; A61K 39/39558
  USPC .................. 530/387.1, 387.3, 391.3
  See application file for complete search history.

(56) References Cited

FOREIGN PATENT DOCUMENTS

WO        2006119062 A2    11/2006
WO    WO 2006119062 A2 *  11/2006

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Rudikoff et al. (Proc. Natl. Acad. Sci. USA. 1982; 79 (6): 1979-1983).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
Winkler et al. (J. Immunol. Oct. 15, 2000; 165 (8): 4505-4514).*
De Pascalis et al. (J. Immunol. 2002; 169 (6): 3076-3084).*
Wu et al. (J. Mol. Biol. Nov. 19, 1999; 294 (1): 151-162).*
Lopez-Requena et al. (Mol. Immunol. 2007; 44: 1015-1028).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Caldas et al., 2003, "Humanization of the anti-CD18 antibody 6.7: an unexpected effect of a framework residue in binding to antigen", Mol. Immunol., 39 (15): 941-952.
Casset et al., 2003, "A peptide mimetic of an anti-CD4 monoclonal antibody by rational design",Biochem. Biophys. Res. Commun., 307 (1): 198-205.
Chien et al., 1989, "Significant structural and functional change of an antigen-binding site by a distant amino acid substitution: Proposal of a structural mechanism", Proc. Natl. Acad. Sci. USA., 86 (14): 5532-5536.
De Pascalis et al., 2002, "Grafting of 'Abbreviated' complementarity-determining regions containing specificity—determining residues essential humanized monoclonal antibody",J. Immunol., (6): 3076-3084.
Giusti et al., 1987, "Somatic diversification of S107 from an antiphosphocholine to an anti-DNA autoantibody is due to a single base change in its heavy chain variable region", Proc. Natl. Acad. Sci. USA., 84 (9): 2926-2930.
Gussowet et al., 1991, "Humanization of monoclonal antibodies", Methods in Enzymology, 203: 99-121.
Holm et al., 2007, "Functional mapping and single chain construction of the anti-cytokeratin 8 monoclonal antibody TS1", Mol. Immunol., 44 (6): 1075-1084.
Lopez-Requena et al., 2007, "Gangliosides, Ab1 and Ab2 antibodies II. Light versus heavy chain: an idiotype-anti-idiotype case study", Mol. Immunol., 44: 1015-1028.
MacCallum et al., 1996, "Antibody-antigen interactions: contact analysis and binding site topography", J. Mol. Biol., 262 (5): 732-745.
Mariuzza et al.,1987, "Annual review of biophysics and biophysical chemistry", Annu. Rev. Biophys. Biophys. Chem., 16: 139-159.
Rudikoff et al., 1982, "Single amino acide substitution altering anti-gen-binding specificty", Proc. Natl. Acad. Sci. USA., 79 (6): 1979-1983.
U.S. Office Action, Jan. 28, 2011, for Paul Chapman, U.S. Appl. No. 12/541,958, filed Aug. 16, 2009.
U.S. Office Action, Jun. 8, 2011, for Paul Chapman, U.S. Appl. No. 12/541,958, filed Aug. 16, 2009.

(Continued)

*Primary Examiner* — Stephen Rawlings
(74) *Attorney, Agent, or Firm* — Law Offices of Albert Wai-Kit Chan, PLLC

(57) ABSTRACT

The present invention is related to complementarity determining region (CDR)-grafted humanized R24 antibodies that bind to the GD3 ganglioside antigen. The humanized antibodies disclosed herein have characteristics that are comparable or superior to the murine R24 antibody, and the humanized antibodies are useful in treating cancer (e.g. Melanoma).

5 Claims, 6 Drawing Sheets

(56) References Cited

OTHER PUBLICATIONS

U.S. Office Action, Nov. 18, 2011, for Paul Chapman, U.S. Appl. No. 12/541,958, filed Aug. 16, 2009.

Vajdos et al., 2002, "Comprehensive functional maps of the antigen-binding site of an anti-ErbB2 antibody obtained with shotgun scanning mutagenesis", J. Mol. Biol., 320 (2): 415-428.

Winkler et al., 2000, "Changing the antigen binding specificity by single point mutations of an anti-p24 (HIV-1) antibody", J. Immunol., 165 (8): 4505-4514.

Wu et al., 1999, "Humanization of a murine monoclonal antibody by simultaneous optimization of framework and CDR residues", J. Mol. Biol., 294 (1): 151-162.

* cited by examiner

SEQUENCE LISTING

<160> NUMBER OF SEQ ID NOS: 25

<210> SEQ ID NO 1
<211> LENGTH: 120
<212> TYPE: PRT
<213> ORGANISM: Homo sapiens
<220> FEATURE:
<223> OTHER INFORMATION: heavy chain variable region

<400> SEQUENCE: 1

```
Gln Val Gln Leu Val Glu Ser Gly Gly Gly Val Val Gln Pro Gly
  1               5                  10                  15

Arg Ser Leu Arg Leu Ser Cys Ala Ala Ser Gly Phe Thr Phe Ser
                 20                  25                  30

Asn Phe Gly Met His Trp Val Arg Gln Ala Pro Gly Lys Gly Leu
             35                  40                  45

Glu Trp Val Ala Tyr Ile Ser Ser Gly Ser Ser Ile Asn Tyr
         50                  55                  60

Ala Asp Thr Val Lys Gly Arg Phe Thr Ile Ser Arg Asp Asn Ser
             65                  70                  75

Lys Asn Thr Leu Tyr Leu Gln Met Asn Ser Leu Arg Ala Glu Asp
             80                  85                  90

Thr Ala Val Tyr Tyr Cys Thr Arg Gly Gly Thr Gly Thr Arg Ser
             95                 100                 105

Leu Tyr Tyr Phe Asp Tyr Trp Gly Gln Gly Thr Thr Val Thr Val
            110                 115                 120
```

<210> SEQ ID NO 2
<211> LENGTH: 107
<212> TYPE: PRT
<213> ORGANISM: Homo sapiens
<220> FEATURE:
<223> OTHER INFORMATION: light chain variable region

<400> SEQUENCE: 2

```
Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Ile Gly
                 20                  25                  30

Asn Phe Leu Asn Trp Tyr Gln Gln Lys Pro Gly Lys Ala Pro Lys
             35                  40                  45

Leu Leu Ile Tyr Tyr Thr Ser Arg Leu Gln Ser Gly Val Pro Ser
             50                  55                  60

Arg Phe Ser Gly Ser Gly Ser Gly Thr Asp Tyr Thr Leu Thr Ile
             65                  70                  75

Ser Ser Leu Gln Pro Glu Asp Phe Ala Thr Tyr Tyr Cys Gln Gln
             80                  85                  90

Gly Lys Thr Leu Pro Tyr Thr Phe Gly Gly Gly Thr Lys Val Glu
             95                 100                 105

Ile Lys
```

<210> SEQ ID NO 3
<211> LENGTH: 120
<212> TYPE: PRT
<213> ORGANISM: Homo sapiens
<220> FEATURE:
<223> OTHER INFORMATION: heavy chain variable region

<400> SEQUENCE: 3

```
Asp Val Gln Leu Val Glu Ser Gly Gly Gly Leu Val Gln Pro Gly
 1               5                  10                  15

Gly Ser Arg Lys Leu Ser Cys Ala Ala Ser Gly Phe Thr Phe Ser
             20                  25                  30

Asn Phe Gly Met His Trp Val Arg Gln Ala Pro Glu Lys Gly Leu
             35                  40                  45

Glu Trp Val Ala Tyr Ile Ser Ser Gly Ser Ser Ile Asn Tyr
             50                  55                  60

Ala Asp Thr Val Lys Gly Arg Phe Thr Ile Ser Arg Asp Asn Pro
             65                  70                  75

Lys Asn Thr Leu Phe Leu Gln Met Thr Ser Leu Arg Ser Glu Asp
             80                  85                  90

Thr Ala Ile Tyr Tyr Cys Thr Arg Gly Gly Thr Gly Thr Arg Ser
             95                 100                 105

Leu Tyr Tyr Phe Asp Tyr Trp Gly Gln Gly Ala Thr Leu Ile Val
            110                 115                 120

<210> SEQ ID NO 4
<211> LENGTH: 107
<212> TYPE: PRT
<213> ORGANISM: Homo sapiens
<220> FEATURE:
<223> OTHER INFORMATION: light chain variable region

<400> SEQUENCE: 4

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Ile Gly
             20                  25                  30

Asn Phe Leu Asn Trp Tyr Gln Gln Lys Pro Gly Lys Ala Pro Lys
             35                  40                  45

Leu Leu Leu Tyr Tyr Thr Ser Arg Leu Gln Ser Gly Val Pro Ser
             50                  55                  60

Arg Phe Ser Gly Ser Gly Ser Gly Thr Asp Tyr Thr Leu Thr Ile
             65                  70                  75

Ser Ser Leu Gln Pro Glu Asp Phe Ala Thr Tyr Tyr Cys Gln Gln
             80                  85                  90

Gly Lys Thr Leu Pro Tyr Thr Phe Gly Gly Gly Thr Lys Val Glu
             95                 100                 105

Ile Lys

<210> SEQ ID NO 5
<211> LENGTH: 5
<212> TYPE: PRT
<213> ORGANISM: Homo sapiens
<220> FEATURE:
<223> OTHER INFORMATION: heavy chain variable region CDR

<400> SEQUENCE: 5

Asn Phe Gly Met His
 1               5

<210> SEQ ID NO 6
<211> LENGTH: 15
<212> TYPE: PRT
<213> ORGANISM: Homo sapiens
<220> FEATURE:
<223> OTHER INFORMATION: heavy chain variable region CDR

<400> SEQUENCE: 6
```

```
Tyr Ile Ser Ser Gly Gly Ser Ser Ile Asn Tyr Ala Asp Thr Val
 1               5                  10                  15
```

<210> SEQ ID NO 7
<211> LENGTH: 13
<212> TYPE: PRT
<213> ORGANISM: Homo sapiens
<220> FEATURE:
<223> OTHER INFORMATION: heavy chain variable region CDR

<400> SEQUENCE: 7

```
Gly Gly Thr Gly Thr Arg Ser Leu Tyr Tyr Phe Asp Tyr
 1               5                  10
```

<210> SEQ ID NO 8
<211> LENGTH: 11
<212> TYPE: PRT
<213> ORGANISM: Homo sapiens
<220> FEATURE:
<223> OTHER INFORMATION: light chain variable region CDR

<400> SEQUENCE: 8

```
Arg Ala Ser Gln Asp Ile Gly Asn Phe Leu Asn
 1               5                  10
```

<210> SEQ ID NO 9
<211> LENGTH: 7
<212> TYPE: PRT
<213> ORGANISM: Homo sapiens
<220> FEATURE:
<223> OTHER INFORMATION: light chain variable region CDR

<400> SEQUENCE: 9

```
Tyr Thr Ser Arg Leu Gln Ser
 1               5
```

<210> SEQ ID NO 10
<211> LENGTH: 9
<212> TYPE: PRT
<213> ORGANISM: Homo sapiens
<220> FEATURE:
<223> OTHER INFORMATION: light chain variable region CDR

<400> SEQUENCE: 10

```
Gln Gln Gly Lys Thr Leu Pro Tyr Thr
 1               5
```

<210> SEQ ID NO 11
<211> LENGTH: 332
<212> TYPE: PRT
<213> ORGANISM: Homo sapiens
<220> FEATURE:
<223> OTHER INFORMATION: heavy chain constant region

<400> SEQUENCE: 11

```
Asp Ile Pro Ser Thr Lys Gly Pro Ser Val Phe Pro Leu Ala Pro
 1               5                  10                  15

Ser Ser Lys Ser Thr Ser Gly Gly Thr Ala Ala Leu Gly Cys Leu
                20                  25                  30

Val Lys Asp Tyr Phe Pro Glu Pro Val Thr Val Ser Trp Asn Ser
                35                  40                  45

Gly Ala Leu Thr Ser Gly Val His Thr Phe Pro Ala Val Leu Gln
                50                  55                  60

Ser Ser Gly Leu Tyr Ser Leu Ser Ser Val Val Thr Val Pro Ser
                65                  70                  75
```

Ser Ser Leu Gly Thr Gln Thr Tyr Ile Cys Asn Val Asn His Lys
            80                  85                  90

Pro Ser Asn Thr Lys Val Asp Lys Val Glu Pro Lys Ser Cys
        95                  100                 105

Asp Lys Thr His Thr Cys Pro Pro Cys Pro Ala Pro Glu Leu Leu
            110                 115                 120

Gly Gly Pro Ser Val Phe Leu Phe Pro Pro Lys Pro Lys Asp Thr
            125                 130                 135

Leu Met Ile Ser Arg Thr Pro Glu Val Thr Cys Val Val Val Asp
            140                 145                 150

Val Ser His Glu Asp Pro Glu Val Lys Phe Asn Trp Tyr Val Asp
            155                 160                 165

Gly Val Glu Val His Asn Ala Lys Thr Lys Pro Arg Glu Glu Gln
            170                 175                 180

Tyr Asn Ser Thr Tyr Arg Val Val Ser Val Leu Thr Val Leu His
            185                 190                 195

Gln Asp Trp Leu Asn Gly Lys Glu Tyr Lys Cys Lys Val Ser Asn
            200                 205                 210

Lys Ala Leu Pro Ala Pro Ile Glu Lys Thr Ile Ser Lys Ala Lys
            215                 220                 225

Gly Gln Pro Arg Glu Pro Gln Val Tyr Thr Leu Pro Pro Ser Arg
            230                 235                 240

Asp Glu Leu Thr Lys Asn Gln Val Ser Leu Thr Cys Leu Val Lys
            245                 250                 255

Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser
            290                 295                 300

Arg Trp Gln Gln Gly Asn Val Phe Ser Cys Ser Val Met His Glu
            305                 310                 315

Ala Leu His Asn His Tyr Thr Gln Lys Ser Leu Ser Leu Ser Pro
            320                 325                 330

Gly Lys

<210> SEQ ID NO 12
<211> LENGTH: 109
<212> TYPE: PRT
<213> ORGANISM: Homo sapiens
<220> FEATURE:
<223> OTHER INFORMATION: light chain constant region

<400> SEQUENCE: 12

Asp Ile Arg Thr Val Ala Ala Pro Ser Val Phe Ile Phe Pro Pro
  1               5                  10                  15

Ser Asp Glu Gln Leu Lys Ser Gly Thr Ala Ser Val Val Cys Leu
            20                  25                  30

Leu Asn Asn Phe Tyr Pro Arg Glu Ala Lys Val Gln Trp Lys Val
            35                  40                  45

Asp Asn Ala Leu Gln Ser Gly Asn Ser Gln Glu Ser Val Thr Glu
            50                  55                  60

Gln Asp Ser Lys Asp Ser Thr Tyr Ser Leu Ser Ser Thr Leu Thr
            65                  70                  75

Leu Ser Lys Ala Asp Tyr Glu Lys His Lys Val Tyr Ala Cys Glu
            80                  85                  90

```
Val Thr His Gln Gly Leu Ser Ser Pro Val Thr Lys Ser Phe Asn
                 95                 100                 105

Arg Gly Glu Cys
```

<210> SEQ ID NO 13
<211> LENGTH: 454
<212> TYPE: PRT
<213> ORGANISM: Homo sapiens
<220> FEATURE:
<223> OTHER INFORMATION: heavy chain region of LD49

<400> SEQUENCE: 13

```
Asp Val Gln Leu Val Glu Ser Gly Gly Leu Val Gln Pro Gly
  1               5                  10                  15

Gly Ser Arg Lys Leu Ser Cys Ala Ala Ser Gly Phe Thr Phe Ser
                 20                  25                  30

Asn Phe Gly Met His Trp Val Arg Gln Ala Pro Glu Lys Gly Leu
                 35                  40                  45

Glu Trp Val Ala Tyr Ile Ser Ser Gly Ser Ser Ile Asn Tyr
                 50                  55                  60

Ala Asp Thr Val Lys Gly Arg Phe Thr Ile Ser Arg Asp Asn Pro
                 65                  70                  75

Lys Asn Thr Leu Phe Leu Gln Met Thr Ser Leu Arg Ser Glu Asp
                 80                  85                  90

Thr Ala Ile Tyr Tyr Cys Thr Arg Gly Thr Gly Thr Arg Ser
                 95                 100                 105

Leu Tyr Tyr Phe Asp Tyr Trp Gly Gln Gly Ala Thr Leu Ile Val
                110                 115                 120

Ser Ser Asp Ile Pro Ser Thr Lys Gly Pro Ser Val Phe Pro Leu
                125                 130                 135

Ala Pro Ser Ser Lys Ser Thr Ser Gly Gly Thr Ala Ala Leu Gly
                140                 145                 150

Cys Leu Val Lys Asp Tyr Phe Pro Glu Pro Val Thr Val Ser Trp
                155                 160                 165

Asn Ser Gly Ala Leu Thr Ser Gly Val His Thr Phe Pro Ala Val
                170                 175                 180

Leu Gln Ser Ser Gly Leu Tyr Ser Leu Ser Ser Val Val Thr Val
                185                 190                 195

Pro Ser Ser Ser Leu Gly Thr Gln Thr Tyr Ile Cys Asn Val Asn
                200                 205                 210

His Lys Pro Ser Asn Thr Lys Val Asp Lys Lys Val Glu Pro Lys
                215                 220                 225

Ser Cys Asp Lys Thr His Thr Cys Pro Pro Cys Pro Ala Pro Glu
                230                 235                 240

Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr
                275                 280                 285

Val Asp Gly Val Glu Val His Asn Ala Lys Thr Lys Pro Arg Glu
                290                 295                 300

Glu Gln Tyr Asn Ser Thr Tyr Arg Val Val Ser Val Leu Thr Val
                305                 310                 315

Leu His Gln Asp Trp Leu Asn Gly Lys Glu Tyr Lys Cys Lys Val
                320                 325                 330
```

-continued

```
Ser Asn Lys Ala Leu Pro Ala Pro Ile Glu Lys Thr Ile Ser Lys
            335                 340                 345

Ala Lys Gly Gln Pro Arg Glu Pro Gln Val Tyr Thr Leu Pro Pro
            350                 355                 360

Ser Arg Asp Glu Leu Thr Lys Asn Gln Val Ser Leu Thr Cys Leu
            365                 370                 375

Val Lys Gly Phe Tyr Pro Ser Asp Ile Ala Val Glu Trp Glu Ser
            380                 385                 390

Asn Gly Gln Pro Glu Asn Asn Tyr Lys Thr Thr Pro Pro Val Leu
            395                 400                 405

Asp Ser Asp Gly Ser Phe Phe Leu Tyr Ser Lys Leu Thr Val Asp
            410                 415                 420

Lys Ser Arg Trp Gln Gln Gly Asn Val Phe Ser Cys Ser Val Met
            425                 430                 435

His Glu Ala Leu His Asn His Tyr Thr Gln Lys Ser Leu Ser Leu
            440                 445                 450

Ser Pro Gly Lys

<210> SEQ ID NO 14
<211> LENGTH: 216
<212> TYPE: PRT
<213> ORGANISM: Homo sapiens
<220> FEATURE:
<223> OTHER INFORMATION: light chain region of LD49

<400> SEQUENCE: 14

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Ile Gly
                20                  25                  30

Asn Phe Leu Asn Trp Tyr Gln Gln Lys Pro Gly Lys Ala Pro Lys
            35                  40                  45

Leu Leu Leu Tyr Tyr Thr Ser Arg Leu Gln Ser Gly Val Pro Ser
            50                  55                  60

Arg Phe Ser Gly Ser Gly Ser Gly Thr Asp Tyr Thr Leu Thr Ile
            65                  70                  75

Ser Ser Leu Gln Pro Glu Asp Phe Ala Thr Tyr Tyr Cys Gln Gln
            80                  85                  90

Gly Lys Thr Leu Pro Tyr Thr Phe Gly Gly Gly Thr Lys Val Glu
            95                  100                 105

Ile Lys Asp Ile Arg Thr Val Ala Ala Pro Ser Val Phe Ile Phe
            110                 115                 120

Pro Pro Ser Asp Glu Gln Leu Lys Ser Gly Thr Ala Ser Val Val
            125                 130                 135

Cys Leu Leu Asn Asn Phe Tyr Pro Arg Glu Ala Lys Val Gln Trp
            140                 145                 150

Lys Val Asp Asn Ala Leu Gln Ser Gly Asn Ser Gln Glu Ser Val
            155                 160                 165

Thr Glu Gln Asp Ser Lys Asp Ser Thr Tyr Ser Leu Ser Ser Thr
            170                 175                 180

Leu Thr Leu Ser Lys Ala Asp Tyr Glu Lys His Lys Val Tyr Ala
            185                 190                 195

Cys Glu Val Thr His Gln Gly Leu Ser Ser Pro Val Thr Lys Ser
            200                 205                 210
```

```
Phe Asn Arg Gly Glu Cys
                215

<210> SEQ ID NO 15
<211> LENGTH: 454
<212> TYPE: PRT
<213> ORGANISM: Homo sapiens
<220> FEATURE:
<223> OTHER INFORMATION: heavy chain region of LD47

<400> SEQUENCE: 15

Gln Val Gln Leu Val Glu Ser Gly Gly Gly Val Val Gln Pro Gly
  1               5                  10                  15

Arg Ser Leu Arg Leu Ser Cys Ala Ala Ser Gly Phe Thr Phe Ser
                 20                  25                  30

Asn Phe Gly Met His Trp Val Arg Gln Ala Pro Gly Lys Gly Leu
                 35                  40                  45

Glu Trp Val Ala Tyr Ile Ser Ser Gly Ser Ser Ile Asn Tyr
                 50                  55                  60

Ala Asp Thr Val Lys Gly Arg Phe Thr Ile Ser Arg Asp Asn Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Thr Arg Gly Gly Thr Gly Thr Arg Ser
                 95                 100                 105

Leu Tyr Tyr Phe Asp Tyr Trp Gly Gln Gly Thr Thr Val Thr Val
                110                 115                 120

Ser Ser Asp Ile Pro Ser Thr Lys Gly Pro Ser Val Phe Pro Leu
                125                 130                 135

Ala Pro Ser Ser Lys Ser Thr Ser Gly Gly Thr Ala Ala Leu Gly
                140                 145                 150

Cys Leu Val Lys Asp Tyr Phe Pro Glu Pro Val Thr Val Ser Trp
                155                 160                 165

Asn Ser Gly Ala Leu Thr Ser Gly Val His Thr Phe Pro Ala Val
                170                 175                 180

Leu Gln Ser Ser Gly Leu Tyr Ser Leu Ser Ser Val Val Thr Val
                185                 190                 195

Pro Ser Ser Ser Leu Gly Thr Gln Thr Tyr Ile Cys Asn Val Asn
                200                 205                 210

His Lys Pro Ser Asn Thr Lys Val Asp Lys Lys Val Glu Pro Lys
                215                 220                 225

Ser Cys Asp Lys Thr His Thr Cys Pro Pro Cys Pro Ala Pro Glu
                230                 235                 240

Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr
                275                 280                 285

Val Asp Gly Val Glu Val His Asn Ala Lys Thr Lys Pro Arg Glu
                290                 295                 300

Glu Gln Tyr Asn Ser Thr Tyr Arg Val Val Ser Val Leu Thr Val
                305                 310                 315

Leu His Gln Asp Trp Leu Asn Gly Lys Glu Tyr Lys Cys Lys Val
                320                 325                 330
```

```
Ser Asn Lys Ala Leu Pro Ala Pro Ile Glu Lys Thr Ile Ser Lys
            335                 340                 345

Ala Lys Gly Gln Pro Arg Glu Pro Gln Val Tyr Thr Leu Pro Pro
            350                 355                 360

Ser Arg Asp Glu Leu Thr Lys Asn Gln Val Ser Leu Thr Cys Leu
            365                 370                 375

Val Lys Gly Phe Tyr Pro Ser Asp Ile Ala Val Glu Trp Glu Ser
            380                 385                 390

Asn Gly Gln Pro Glu Asn Asn Tyr Lys Thr Thr Pro Pro Val Leu
            395                 400                 405

Asp Ser Asp Gly Ser Phe Phe Leu Tyr Ser Lys Leu Thr Val Asp
            410                 415                 420

Lys Ser Arg Trp Gln Gln Gly Asn Val Phe Ser Cys Ser Val Met
            425                 430                 435

His Glu Ala Leu His Asn His Tyr Thr Gln Lys Ser Leu Ser Leu
            440                 445                 450

Ser Pro Gly Lys

<210> SEQ ID NO 16
<211> LENGTH: 216
<212> TYPE: PRT
<213> ORGANISM: Homo sapiens
<220> FEATURE:
<223> OTHER INFORMATION: light chain region of LD47

<400> SEQUENCE: 16

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Ile Gly
            20                  25                  30

Asn Phe Leu Asn Trp Tyr Gln Gln Lys Pro Gly Lys Ala Pro Lys
            35                  40                  45

Leu Leu Ile Tyr Tyr Thr Ser Arg Leu Gln Ser Gly Val Pro Ser
            50                  55                  60

Arg Phe Ser Gly Ser Gly Ser Gly Thr Asp Tyr Thr Leu Thr Ile
            65                  70                  75

Ser Ser Leu Gln Pro Glu Asp Phe Ala Thr Tyr Tyr Cys Gln Gln
            80                  85                  90

Gly Lys Thr Leu Pro Tyr Thr Phe Gly Gly Gly Thr Lys Val Glu
            95                  100                 105

Ile Lys Asp Ile Arg Thr Val Ala Ala Pro Ser Val Phe Ile Phe
            110                 115                 120

Pro Pro Ser Asp Glu Gln Leu Lys Ser Gly Thr Ala Ser Val Val
            125                 130                 135

Cys Leu Leu Asn Asn Phe Tyr Pro Arg Glu Ala Lys Val Gln Trp
            140                 145                 150

Lys Val Asp Asn Ala Leu Gln Ser Gly Asn Ser Gln Glu Ser Val
            155                 160                 165

Thr Glu Gln Asp Ser Lys Asp Ser Thr Tyr Ser Leu Ser Ser Thr
            170                 175                 180

Leu Thr Leu Ser Lys Ala Asp Tyr Glu Lys His Lys Val Tyr Ala
            185                 190                 195

Cys Glu Val Thr His Gln Gly Leu Ser Ser Pro Val Thr Lys Ser
            200                 205                 210
```

```
Phe Asn Arg Gly Glu Cys
            215

<210> SEQ ID NO 17
<211> LENGTH: 107
<212> TYPE: PRT
<213> ORGANISM: Homo sapiens
<220> FEATURE:
<223> OTHER INFORMATION: CDR-grafted vk for LD47

<400> SEQUENCE: 17

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Ile Gly
                20                  25                  30

Asn Phe Leu Asn Trp Tyr Gln Gln Lys Pro Gly Lys Ala Pro Lys
                35                  40                  45

Leu Leu Ile Tyr Tyr Thr Ser Arg Leu Gln Ser Gly Val Pro Ser
                50                  55                  60

Arg Phe Ser Gly Ser Gly Ser Gly Thr Asp Tyr Thr Leu Thr Ile
                65                  70                  75

Ser Ser Leu Gln Pro Glu Asp Phe Ala Thr Tyr Tyr Cys Gln Gln
                80                  85                  90

Gly Lys Thr Leu Pro Tyr Thr Phe Gly Gly Gly Thr Lys Val Glu
                95                  100                 105

Ile Lys

<210> SEQ ID NO 18
<211> LENGTH: 107
<212> TYPE: PRT
<213> ORGANISM: Homo sapiens
<220> FEATURE:
<223> OTHER INFORMATION: CDR-grafted vk for LD49

<400> SEQUENCE: 18

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Ile Gly
                20                  25                  30

Asn Phe Leu Asn Trp Tyr Gln Gln Lys Pro Gly Lys Ala Pro Lys
                35                  40                  45

Leu Leu Leu Tyr Tyr Thr Ser Arg Leu Gln Ser Gly Val Pro Ser
                50                  55                  60

Arg Phe Ser Gly Ser Gly Ser Gly Thr Asp Tyr Thr Leu Thr Ile
                65                  70                  75

Ser Ser Leu Gln Pro Glu Asp Phe Ala Thr Tyr Tyr Cys Gln Gln
                80                  85                  90

Gly Lys Thr Leu Pro Tyr Thr Phe Gly Gly Gly Thr Lys Val Glu
                95                  100                 105

Ile Lys

<210> SEQ ID NO 19
<211> LENGTH: 122
<212> TYPE: PRT
<213> ORGANISM: Homo sapiens
<220> FEATURE:
<223> OTHER INFORMATION: CDR-grafted vh for LD47

<400> SEQUENCE: 19
```

-continued

```
Gln Val Gln Leu Val Glu Ser Gly Gly Gly Val Val Gln Pro Gly
  1               5                  10                  15

Arg Ser Leu Arg Leu Ser Cys Ala Ala Ser Gly Phe Thr Phe Ser
             20                  25                  30

Asn Phe Gly Met His Trp Val Arg Gln Ala Pro Gly Lys Gly Leu
             35                  40                  45

Glu Trp Val Ala Tyr Ile Ser Ser Gly Ser Ser Ile Asn Tyr
             50                  55                  60

Ala Asp Thr Val Lys Gly Arg Phe Thr Ile Ser Arg Asp Asn Ser
             65                  70                  75

Lys Asn Thr Leu Tyr Leu Gln Met Asn Ser Leu Arg Ala Glu Asp
             80                  85                  90

Thr Ala Val Tyr Tyr Cys Thr Arg Gly Gly Thr Gly Thr Arg Ser
             95                 100                 105

Leu Tyr Tyr Phe Asp Tyr Trp Gly Gln Gly Thr Thr Val Thr Val
            110                 115                 120

Ser Ser
```

<210> SEQ ID NO 20
<211> LENGTH: 122
<212> TYPE: PRT
<213> ORGANISM: Homo sapiens
<220> FEATURE:
<223> OTHER INFORMATION: chimeric gamma chain for LD47

<400> SEQUENCE: 20

```
Asp Val Gln Leu Val Glu Ser Gly Gly Gly Leu Val Gln Pro Gly
  1               5                  10                  15

Gly Ser Arg Lys Leu Ser Cys Ala Ala Ser Gly Phe Thr Phe Ser
             20                  25                  30

Asn Phe Gly Met His Trp Val Arg Gln Ala Pro Glu Lys Gly Leu
             35                  40                  45

Glu Trp Val Ala Tyr Ile Ser Ser Gly Ser Ser Ile Asn Tyr
             50                  55                  60

Ala Asp Thr Val Lys Gly Arg Phe Thr Ile Ser Arg Asp Asn Pro
             65                  70                  75

Lys Asn Thr Leu Phe Leu Gln Met Thr Ser Leu Arg Ser Glu Asp
             80                  85                  90

Thr Ala Ile Tyr Tyr Cys Thr Arg Gly Gly Thr Gly Thr Arg Ser
             95                 100                 105

Leu Tyr Tyr Phe Asp Tyr Trp Gly Gln Gly Ala Thr Leu Ile Val
            110                 115                 120

Ser Ser
```

<210> SEQ ID NO 21
<211> LENGTH: 107
<212> TYPE: PRT
<213> ORGANISM: Homo sapiens
<220> FEATURE:
<223> OTHER INFORMATION: CDR-grafted kappa chain for LD47

<400> SEQUENCE: 21

```
Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Ile Gly
             20                  25                  30
```

```
Asn Phe Leu Asn Trp Tyr Gln Gln Lys Pro Gly Lys Ala Pro Lys
                35                  40                  45

Leu Leu Ile Tyr Tyr Thr Ser Arg Leu Gln Ser Gly Val Pro Ser
        50                  55                  60

Arg Phe Ser Gly Ser Gly Ser Gly Thr Asp Tyr Thr Leu Thr Ile
65                  70                  75

Ser Ser Leu Gln Pro Glu Asp Phe Ala Thr Tyr Tyr Cys Gln Gln
            80                  85                  90

Gly Lys Thr Leu Pro Tyr Thr Phe Gly Gly Gly Thr Lys Val Glu
                95                  100                 105

Ile Lys

<210> SEQ ID NO 22
<211> LENGTH: 122
<212> TYPE: PRT
<213> ORGANISM: Homo sapiens
<220> FEATURE:
<223> OTHER INFORMATION: CDR-grafted gamma chain for LD49

<400> SEQUENCE: 22

Gln Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser
                20                  25                  30

Asn Phe Gly Met His Trp Val Arg Gln Ala Pro Gly Lys Gly Leu
                35                  40                  45

Glu Trp Val Ala Tyr Ile Ser Ser Gly Ser Ser Ile Asn Tyr
        50                  55                  60

Ala Asp Thr Val Lys Gly Arg Phe Thr Ile Ser Arg Asp Asn Ser
65                  70                  75

Lys Asn Thr Leu Tyr Leu Gln Met Asn Ser Leu Arg Ala Glu Asp
            80                  85                  90

Thr Ala Val Tyr Tyr Cys Thr Arg Gly Gly Thr Gly Thr Arg Ser
                95                  100                 105

Leu Tyr Tyr Phe Asp Tyr Trp Gly Gln Gly Ile Thr Val Thr Val
                110                 115                 120

Ser Ser

<210> SEQ ID NO 23
<211> LENGTH: 107
<212> TYPE: PRT
<213> ORGANISM: Homo sapiens
<220> FEATURE:
<223> OTHER INFORMATION: CDR-grafted kappa chain for LD49

<400> SEQUENCE: 23

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Gly
                20                  25                  30

Asn Phe Leu Asn Trp Tyr Gln Gln Lys Pro Gly Lys Ala Pro Lys
                35                  40                  45

Leu Leu Leu Tyr Tyr Thr Ser Arg Leu Gln Ser Gly Val Pro Ser
        50                  55                  60

Arg Phe Ser Gly Ser Gly Ser Gly Thr Asp Tyr Thr Leu Thr Ile
65                  70                  75
```

-continued

Ser Ser Leu Gln Pro Glu Asp Phe Ala Thr Tyr Tyr Cys Gln Gln
            80                  85                  90

Gly Lys Thr Leu Pro Tyr Thr Phe Gly Gly Gly Thr Lys Val Glu
            95                  100                 105

Ile Lys

<210> SEQ ID NO 24
<211> LENGTH: 122
<212> TYPE: PRT
<213> ORGANISM: Homo sapiens
<220> FEATURE:
<223> OTHER INFORMATION: heavy chain variable region

<400> SEQUENCE: 24

Gln Val Gln Leu Val Glu Ser Gly Gly Gly Val Val Gln Pro Gly
 1               5                   10                  15

Arg Ser Leu Arg Leu Ser Cys Ala Ala Ser Gly Phe Thr Phe Ser
                20                  25                  30

Asn Phe Gly Met His Trp Val Arg Gln Ala Pro Gly Lys Gly Leu
            35                  40                  45

Glu Trp Val Ala Tyr Ile Ser Ser Gly Ser Ser Ile Asn Tyr
        50                  55                  60

Ala Asp Thr Val Lys Gly Arg Phe Thr Ile Ser Arg Asp Asn Ser
            65                  70                  75

Lys Asn Thr Leu Tyr Leu Gln Met Asn Ser Leu Arg Ala Glu Asp
            80                  85                  90

Thr Ala Val Tyr Tyr Cys Thr Arg Gly Gly Thr Gly Thr Arg Ser
            95                  100                 105

Leu Tyr Tyr Phe Asp Tyr Trp Gly Gln Gly Thr Thr Val Thr Val
            110                 115                 120

Ser Ser

<210> SEQ ID NO 25
<211> LENGTH: 122
<212> TYPE: PRT
<213> ORGANISM: Homo sapiens
<220> FEATURE:
<223> OTHER INFORMATION: heavy chain variable region

<400> SEQUENCE: 25

Asp Val Gln Leu Val Glu Ser Gly Gly Gly Leu Val Gln Pro Gly
 1               5                   10                  15

Gly Ser Arg Lys Leu Ser Cys Ala Ala Ser Gly Phe Thr Phe Ser
                20                  25                  30

Asn Phe Gly Met His Trp Val Arg Gln Ala Pro Glu Lys Gly Leu
            35                  40                  45

Glu Trp Val Ala Tyr Ile Ser Ser Gly Ser Ser Ile Asn Tyr
        50                  55                  60

Ala Asp Thr Val Lys Gly Arg Phe Thr Ile Ser Arg Asp Asn Pro
            65                  70                  75

Lys Asn Thr Leu Phe Leu Gln Met Thr Ser Leu Arg Ser Glu Asp
            80                  85                  90

Thr Ala Ile Tyr Tyr Cys Thr Arg Gly Gly Thr Gly Thr Arg Ser
            95                  100                 105

Leu Tyr Tyr Phe Asp Tyr Trp Gly Gln Gly Ala Thr Leu Ile Val
            110                 115                 120

Ser Ser

ANTI GANGLIOSIDE GD3 ANTIBODIES AND USES THEREOF

This application is a divisional application of U.S. Ser. No. 12/541,958, filed on Aug. 16, 2008, now issued as U.S. Pat. No. 8,207,308, which is a continuation-in-part of International application No. PCT/US2008/54220, filed Feb. 18, 2008, which claims the benefit of priority of U.S. Ser. No. 60/901,875, filed Feb. 16, 2007. The entire contents and disclosures of the preceding applications are incorporated by reference into this application.

Throughout this application, various references or publications are cited. Disclosures of these references or publications in their entireties are hereby incorporated by reference into this application in order to more fully describe the state of the art to which this invention pertains.

FIELD OF THE INVENTION

The present invention relates to the making and using of humanized antibodies that bind to the ganglioside GD3 antigen.

BACKGROUND OF THE INVENTION

The GD3 ganglioside is a glycosphingolipid that is over expressed on melanoma cells. Thus, the GD3 ganglioside is an attractive target for immunotherapy of melanoma. At present, there is no effective therapeutic regimen approved for advanced melanoma which results in a sustained benefit. The treatment guidelines that exist in most countries focus primarily on surgery to remove malignant melanoma and there is little if any guidance on the selection of chemotherapy or immunotherapy regimens. Even between experts, there is little if any agreement on treatment options.

In Stages I-III of the disease, surgery is generally the first line treatment, followed by adjuvant (post-resection) treatment using recombinant IFN alpha2 products (Schering Plough's Intron A™), or various combinations of chemotherapeutic regimens, although there is no demonstrated sustained survival benefit in the rIFN treatment regimens. For Stage IV patients, where the disease has metastasised, treatments used tend to be chemotherapy or high-dose IFN alpha2, but the prognosis for such patients is very poor, with a very low (9%) response rate and a median survival rate of six to nine months. A significant proportion of Stage II+III patients also are at risk of developing metastatic disease. Due to the bleak outlook for Stage IV patients, most are enrolled in clinical trials for developing therapeutics.

Previous work has identified a mouse IgG3 monoclonal antibody, known as R24, that binds to the GD3 ganglioside. This antibody has been shown to exhibit a phenomenon known as homophilic binding, whereby the antibodies bind to each other. Furthermore, although IgG3 mouse antibodies are not particularly efficient at fixing human complement, it has been found that R24 was active in vitro with respect to complement-dependent cytotoxicity (CDC) and antibody-dependent cellular cytotoxicity (ADCC) (Chapman et al., J. Immunol. (1990) 145(3): 891-898).

The murine R24 antibody has been used in the treatment of malignant melanoma. A considerable number of clinical trials have been conducted with the murine R24 antibody in patients with late stage malignant melanoma, either alone or in combination with other agents, and these have had some success with regards to tumour regression. However, the antibody elicited some immunogenic responses in a significant proportion of patients owing to the fact that it was murine in nature (Bajorin, D. F. et al., Melanoma Research (1992) 2 (5-6): 355-362). For this reason, dosing was restricted and the treatment regimens were not able to be optimised.

A chimeric mouse-human version of the R24 antibody has been generated. However, this chimeric antibody exhibited a substantially lower level of binding to the GD3-binding site compared to the murine R24 antibody. In addition, while the chimeric antibody maintained the characteristics of homophilic binding and fixing human complement, the efficiency of ADCC was slightly reduced. This chimeric antibody is formed from entire murine antibody heavy chain and light chain variable regions engineered onto human heavy chain and light chain constant regions as described in Chapman et al., Cancer Immunol. Immunother. (1994) 39: 198-204.

There are other known monoclonal mouse antibodies that bind to the GD3 ganglioside, such as the KM-641 antibody produced by a hybridoma KM.-641. Chimeric versions of these antibodies, e.g., KM-871, are also known (see U.S. Pat. No. 6,437,098). These chimeric versions are also formed from entire murine antibody heavy chain and light chain variable regions engineered onto human heavy chain and light chain constant regions.

Most therapies in development are targeting the earlier, non-metastatic stages of malignant melanoma, owing to the difficulties in obtaining a response when the disease has metastasised. There are very few immunotherapeutics targeting Stage IV melanoma.

Thus, there is clearly a significant demand for an effective treatment, particularly for advanced malignant melanoma, but also melanoma generally.

SUMMARY OF THE INVENTION

The present invention provides an antibody comprising a heavy chain variable region comprising the following amino acid sequence: Q/DVQLVESGGGV/LVQPGR/GSL/RR/KLSCAASGFTFSNFGMHWVRQAPG/EK-GLEWVAYISSGGSSINYADTVKGRFTISRDNS/PKNTLY/FLQMN/TSLRA/SEDTAV/IYYCTRGGTGTRSLYYFDYWGQGT/ATV/LT/IV (SEQ ID NO:1 or 3), a fragment of said sequence or a sequence that is homologous thereto; and a light chain variable region comprising the following amino acid sequence: DIQMTQSPSSLSASVGDRVTITCRASQ-DIGNFLNWYQQKPGKAPKLLI/LYYTSRLQSGVPSRF-SGSGSGTDYTLTISSLQPEDFATYYC-QQGKTLPYTFGGGTKVEIK (SEQ ID NO:2 or 4), a fragment of said sequence or a sequence that is homologous thereto.

In one embodiment there is provided an antibody comprising a heavy chain variable region comprising the following amino acid sequence: Q/DVQLVESGGGV/LVQPGR/GSL/RR/KLSCAASGFTFSNFGMHWVRQAPG/EK-GLEWVAYISSGGSSINYADTVKGRFTISRDNS/PKNTLY/FLQMN/TSLRA/SEDTAV/IYYCTRGGTGTRSLYYFDYWGQGT/ATV/LT/IV SS (SEQ ID NO:24 or 25), a fragment of said sequence or a sequence that is homologous thereto; and a light chain variable region comprising the following amino acid sequence: DIQMTQSPSSLSASVGDRVTITCRASQ-DIGNFLNWYQQKPGKAPKLLI/LYYTSRLQSGVPSRF-SGSGSGTDYTLTISSLQPEDFATYYC-QQGKTLPYTFGGGTKVEIK (SEQ ID NO:2 or 4), a fragment of said sequence or a sequence that is homologous thereto.

In one embodiment, the antibody of the present invention comprises a heavy chain variable region comprising the following amino acid sequence: QVQLVESGGG VVQPGRSLRL SCAASGFTFS NFGMHWVRQA PGK-GLEWVAY ISSGGSSINY ADTVKGRFTI SRDNSKNTLY LQMNSLRAED TAVYYCTRGG TGTRSLYYFD YWGQGTTVTV (SEQ ID NO:1), and a light chain variable region comprising the following amino acid sequence: DIQMTQSPSS LSASVGDRVT ITCRASQDIG NFLNW-YQQKP GKAPKLLIYY TSRLQSGVPS RFSGSGSGTD YTLTISSLQP EDFATYYCQQ GKTLPYTFGG GTKVEIK (SEQ ID NO:2).

In another embodiment, the antibody of the present invention comprises a heavy chain variable region comprising the following amino acid sequence: DVQLVESGGG LVQPGGSRKL SCAASGFTFS NFGMHWVRQA PEKGLEWVAY ISSGGSSINY ADTVKGRFTI SRDNP-KNTLF LQMTSLRSED TAIYYCTRGG TGTRSLYYFD YWGQGATLIV (SEQ ID NO:3); and a light chain variable region comprising the following amino acid sequence: DIQMTQSPSS LSASVGDRVT ITCRASQDIG NFLNW-YQQKP GKAPKLLLYY TSRLQSGVPS RFSGSGSGTD YTLTISSLQP EDFATYYCQQ GKTLPYTFGG GTKVEIK (SEQ ID NO:4).

The present invention also provides compositions comprising the antibodies disclosed herein. In one embodiment, the antibodies are radio-labeled. In another embodiment, the compositions further comprise a therapeutic or an anti-melanoma drug. Examples of the therapeutic or anti-melanoma drug include, but are not limited to, one or more cytotoxic drugs, interleukins, drugs that activate the immune system or lymphocytes, antibodies that bind to melanoma, antibodies that bind to tumor matrix, antibodies designed to inhibit vascular structures, and drugs that block critical biochemical pathways in melanoma. Accordingly, examples of the therapeutic or anti-melanoma drug include, but are not limited to, dacarbazine, fotemustine, carmustine, lomustine, temozolomide, amifostine, cisplatin, carboplatin, TAXOL, TAXOTERE, tamoxifen, vinblastin, vincristine, DHFR inhibitors (e.g. piritrexim isethionate), interleukin 2 including aldesleukin, interferon alpha, interferon alpha-2b, other anti-tumor antibodies or kinase inhibitors such as tyrosine kinase inhibitors or serine/threonin kinase inhibitors.

The present invention also provides isolated nucleic acid sequences encoding the antibodies disclosed herein, as well as vectors comprising the nucleic acid sequences, and host cells comprising the vectors. In one embodiment, the host cells are avian cells, plant cells, algae, fungal cells, or animal cells.

The present invention also provides methods of using the antibodies disclosed herein to treat malignant diseases such as malignant melanoma.

DETAILED DESCRIPTION OF THE INVENTION

Figure 1:
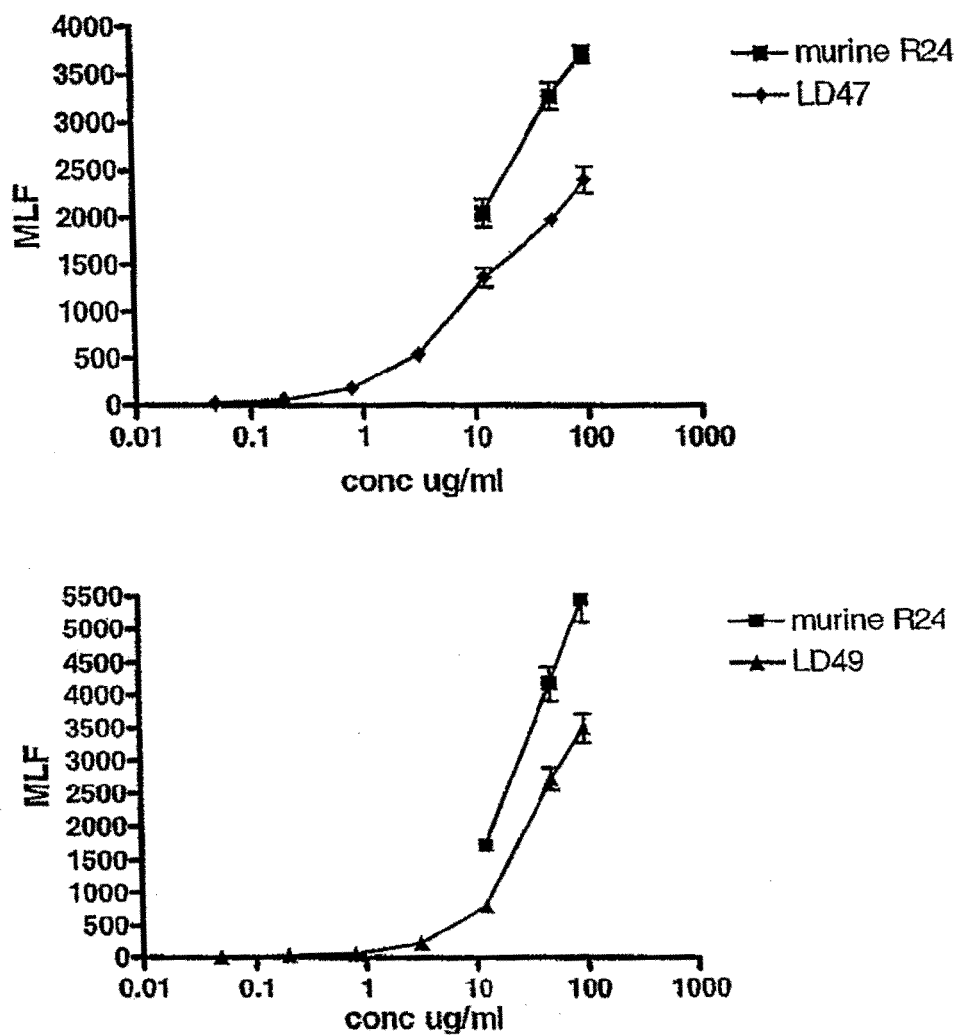
FIG. 1 illustrates binding of humanized R24 antibodies to MeWo human melanoma cell line over a range of antibody concentrations 100 ug/ml-0.0125 ug/ml, each concentration was performed in triplicate and the results are presented as mean % MLF+/−standard error.

Humanization (CDR-grafting) is now a well-established technique for reducing the immunogenicity of monoclonal antibodies (mAbs) from xenogeneic sources (commonly rodent), and for improving their activation of the human immune system. The technique involves grafting rodent antibody complementarity-determining regions (CDRs) into human antibody variable domain frameworks. However, such a technique does not always reconstitute the binding affinity and specificity of the original mAb. The design of the humanized antibody is important for reproduction of the function of the original donor antibody, and includes various choices: the extents of the CDRs, the human frameworks to use and the substitution of residues from the rodent mAb into the human framework regions (back mutations). As such the procedure is complicated and it is difficult to predict success.

It has now been surprisingly found that R24 complementarity determining region (CDR)-grafted humanized antibodies have characteristics that are comparable or superior to the murine R24 antibody including exhibiting similar binding affinity to the GD3 ganglioside antigen.

According to one aspect of the present invention, there is provided an antibody comprising a heavy chain variable region comprising the following amino acid sequence:

(SEQ ID NO: 1 or 3)
Q/DVQLVESGGGV/LVQPGR/GSL/RR/KLSCAASGFTFSNFGMHWVRQAPG/

EKGLEWVAYISSGGSSINYADTVKGRFTISRDNS/PKNTLY/FLQMN/TSLRA/SEDTAV/

IYYCTRGGTGTRSLYYFDYWGQGT/ATV/LT/IV, a fragment of said sequence or a sequence that is homologous thereto; and a light chain variable region comprising the following amino acid sequence:

(SEQ ID NO: 2 or 4)
DIQMTQSPSSLSASVGDRVTITCRASQDIGNFLNWYQQKPGKAPKLLI/

LYYTSRLQSGVPSRFSGSGSGTDYTLTISSLQPEDFATYYCQQGKTLPY

TFGGGTKVEIK, a fragment of said sequence or a sequence that is homologous thereto.

An antibody of the present invention can have a heavy chain variable region with the amino acids glutamine or aspartic acid at position 1, valine or leucine at position 11, arginine or glycine at position 16, leucine or arginine at position 18, arginine or lysine at position 19, glycine or glutamic acid at position 42, serine or proline at position 74, tyrosine or phenylalanine at position 79, asparagine or threonine at position 82a, alanine or serine at position 84, valine or isoleucine at position 89, threonine or alanine at position 107, valine or leucine at position 109 and threonine or isoleucine at position 110 and a light chain variable region with the amino acids isoleucine or leucine at position 48. The positions of the amino acids are described with reference to Kabat numbering as described in Kabat, E. A. et al., Sequences of Proteins of Immunological Interest, NIH publication (1991) Fifth edition, No. 91-3242.

In one embodiment, an antibody of the present invention comprises a heavy chain variable region comprising the following amino acid sequence:

(SEQ ID NO: 1)
QVQLVESGGG VVQPGRSLRL SCAASGFTFS NFGMHWVRQA

PGKGLEWVAY ISSGGSSINY ADTVKGRFTI SRDNSKNTLY

LQMNSLRAED TAVYYCTRGG TGTRSLYYFD YWGQGTTVTV;

and a light chain variable region comprising the following amino acid sequence:

(SEQ ID NO: 2)
DIQMTQSPSS LSASVGDRVT ITCRASQDIG NFLNWYQQKP

GKAPKLLIYY TSRLQSGVPS RFSGSGSGTD YTLTISSLQP

EDFATYYCQQ GKTLPYTFGG GTKVEIK

In another embodiment, an antibody of the present invention comprises a heavy chain variable region comprising the following amino acid sequence:

(SEQ ID NO: 3)
DVQLVESGGG LVQPGGSRKL SCAASGFTFS NFGMHWVRQA

PEKGLEWVAY ISSGGSSINY ADTVKGRFTI SRDNPKNTLF

LQMTSLRSED TAIYYCTRGG TGTRSLYYFD YWGQGATLIV;

and a light chain variable region comprising the following amino acid sequence:

(SEQ ID NO: 4)
DIQMTQSPSS LSASVGDRVT ITCRASQDIG NFLNWYQQKP

GKAPKLLLYY TSRLQSGVPS RFSGSGSGTD YTLTISSLQP

EDFATYYCQQ GKTLPYTFGG GTKVEIK

In one embodiment, an antibody of the present invention comprises a heavy chain variable region comprising the following amino acid sequence:

(SEQ ID NO: 1)
QVQLVESGGG VVQPGRSLRL SCAASGFTFS NFGMHWVRQA

PGKGLEWVAY ISSGGSSINY ADTVKGRFTI SRDNSKNTLY

LQMNSLRAED TAVYYCTRGG TGTRSLYYFD YWGQGTTVTV;

and a light chain variable region comprising the following amino acid sequence:

(SEQ ID NO: 4)
DIQMTQSPSS LSASVGDRVT ITCRASQDIG NFLNWYQQKP

GKAPKLLLYY TSRLQSGVPS RFSGSGSGTD YTLTISSLQP

EDFATYYCQQ GKTLPYTFGG GTKVEIK

In another embodiment, an antibody of the present invention comprises a heavy chain variable region comprising the following amino acid sequence:

(SEQ ID NO: 3)
DVQLVESGGG LVQPGGSRKL SCAASGFTFS NFGMHWVRQA

PEKGLEWVAY ISSGGSSINY ADTVKGRFTI SRDNPKNTLF

LQMTSLRSED TAIYYCTRGG TGTRSLYYFD YWGQGATLIV;

and a light chain variable region comprising the following amino acid sequence:

(SEQ ID NO: 2)
DIQMTQSPSS LSASVGDRVT ITCRASQDIG NFLNWYQQKP

GKAPKLLIYY TSRLQSGVPS RFSGSGSGTD YTLTISSLQP

EDFATYYCQQ GKTLPYTFGG GTKVEIK

An antibody is a protein made up of four polypeptide chains: two identical heavy (also known as gamma for IgG isotype antibodies) chains and two identical light (also known as kappa or lambda) chains connected by disulfide bonds. Each heavy and light chain has a constant region and a variable region. The CDRs are found within the variable regions. The CDRs will be in contact with an antigen, when an antibody binds to an antigen.

The antibodies of the present invention recognize and bind to the GD3 ganglioside antigen. Antibodies of the present invention may comprise at least one human heavy chain variable region or at least one human light chain variable region in which the human CDR sequence is replaced by R24 murine antibody CDR sequence. In addition, the antibody of the invention can contain 1, 2, 3, 4 or 5 mutations back to the murine R24 antibody sequence in the non-CDR human heavy chain or human light chain variable regions The antibodies of the invention as defined above comprise complementarity determining regions (CDRs) with the following amino acid sequences in the heavy chain variable region: NFGMH (SEQ ID NO:5), YISSGGSSINYADTV (SEQ ID NO:6) and GGTGTRSLYYFDY (SEQ ID NO:7); and the following amino acid sequences in the light chain variable region: RASQDIGNFLN (SEQ ID NO:8), YTSRLQS (SEQ ID NO:9) and QQGKTLPYT (SEQ ID NO:10).

A fragment of an antibody described above comprises at least one of the CDRs described above and retains the ability to bind to the GD3 ganglioside antigen. Specific examples of binding fragments are i) the Fab fragment that consists of the VL, VH, CL and CH1 domains; ii) the Fd fragment consisting of the VH and CH1 domains; iii) the Fv fragment consisting of VL and VH domains; iv) the dAB fragment (Ward, E. S. et al., Nature (1989) 341:544-546), which consists of a VH domain; v) isolated CDR regions; vi) F(ab')2 fragments, a bivalent fragment comprising two linked Fab fragments, vii) single chain Fv molecules (scFv), wherein a VH domain and a VL domain are linked by a peptide linker which allows the two regions to associate to form an antigen binding site (Bird et al., Science (1988) 242:423-426 and Huston et al., PNAS USA (1988) 85:5879-5883); viii) bispecific single chain Fv dimers (PCT/US92/09965) and (ix) "diabodies", multivalent or multispecific fragments constructed by gene fusion (W094/13804 and Hollinger et al., (1993) Proc. Natl. Acad. Sci. USA, 90:6444-6448).

A fragment of an antibody of the present invention is a stretch of amino acid residues of at least 5 to 7 contiguous amino acids, often at least 7 to 9 contiguous amino acids, typically at least about 9 to 13 contiguous amino acids and preferably at least about 20 to 30 or more contiguous amino acids and most preferably at least about 30 to 40 or more consecutive amino acids.

One aspect of the present invention extends to a heavy chain variable region with an amino acid sequence that is at least 80%, 85%, 90%, 95%, 96%, 97%, 98%, 99%, 99.5% or 99.9% homologous to the sequence of the heavy chain variable region described above. Preferably the heavy chain variable region is 90% homologous to the sequence of the heavy chain variable region described above.

One aspect of the present invention extends to a light chain variable region with an amino acid sequence that is at least 80%, 85%, 90%, 95%, 96%, 97%, 98%, 99%, 99.5% or 99.9% homologous to the sequence of the light chain variable region described above. Preferably the light chain variable region is 90% homologous to the sequence of the light chain variable region described above.

The antibodies of the present invention further comprise a heavy chain constant region and a light chain constant region of a human antibody. Human heavy chain constant regions may be from one of five classes (IgM, IgG, IgA, IgE or IgD) or their sub-classes (IgG1, IgG2, IgG3, IgG4, IgA1 or IgA2). Light chain constant regions may be from the kappa or lambda classes. The antibodies of the invention can be human IgG1/kappa antibodies, for example. Heavy chain and light chain constant regions from non-human antibodies may also be used with the variable domains of the invention, if those constant regions have been deimmunized for use in man.

In one embodiment, the heavy chain constant region of the antibodies may comprise the following amino acid sequence:

```
                                      (SEQ ID NO: 11)
DIPSTKGP SVFPLAPSSK STSGGTAALG CLVKDYFPEP

VTVSWNSGAL TSGVHTFPAV LQSSGLYSLS SVVTVPSSSL

GTQTYICNVN HKPSNTKVDK KVEPKSCDKT HTCPPCPAPE

LLGGPSVFLF PPKPKDTLMI SRTPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SRDELTKNQV SLTCLVKGFY PSDIAVEWES NGQPENNYKT
```
-continued
```
TPPVLDSDGS FFLYSKLTVD KSRWQQGNVF SCSVMHEALH

NHYTQKSLSL SPGK
```

In one embodiment, the light chain constant region of the antibodies may comprise the following amino acid sequence:

```
                                      (SEQ ID NO: 12)
DIR TVAAPSVFIF PPSDEQLKSG TASVVCLLNN FYPREAKVQW

KVDNALQSGN SQESVTEQDS KDSTYSLSST LTLSKADYEK

HKVYACEVTH QGLSSPVTKS FNRGEC
```

A further embodiment of the invention is an antibody which comprises a heavy chain region comprising the following amino acid sequence:

```
                                 (SEQ ID NO: 13 or 15)
Q/DVQLVESGGG V/LVQPGR/GSL/RR/KL SCAASGFTFS

NFGMHWVRQA PG/EKGLEWVAY ISSGGSSINY ADTVKGRFTI

SRDNS/PKNTLY/F LQMN/TSLRA/SED TAV/IYYCTRGG

TGTRSLYYFD YWGQGT/ATV/LT/IV SSDIPSTKGP

SVFPLAPSSK STSGGTAALG CLVKDYFPEP VTVSWNSGAL

TSGVHTFPAV LQSSGLYSLS SVVTVPSSSL GTQTYICNVN

HKPSNTKVDK KVEPKSCDKT HTCPPCPAPE LLGGPSVFLF

PPKPKDTLMI SRTPEVTCVV VDVSHEDPEV KFNWYVDGVE

VHNAKTKPRE EQYNSTYRVV SVLTVLHQDW LNGKEYKCKV

SNKALPAPIE KTISKAKGQP REPQVYTLPP SRDELTKNQV

SLTCLVKGFY PSDIAVEWES NGQPENNYKT TPPVLDSDGS

FFLYSKLTVD KSRWQQGNVF SCSVMHEALH NHYTQKSLSL SPGK
``` and a light chain region comprising the following amino acid sequence:

```
                                 (SEQ ID NO: 14 or 16)
DIQMTQSPSS LSASVGDRVT ITCRASQDIG NFLNWYQQKP

GKAPKLLI/LYY TSRLQSGVPS RFSGSGSGTD YTLTISSLQP

EDFATYYCQQ GKTLPYTFGG GTKVEIKDIR TVAAPSVFIF

PPSDEQLKSG TASVVCLLNN FYPREAKVQW KVDNALQSGN

SQESVTEQDS KDSTYSLSST LTLSKADYEK HKVYACEVTH

QGLSSPVTKS FNRGEC
```

This embodiment of the invention extends to a heavy chain region with an amino acid sequence that is at least 80%, 85%, 90%, 95%, 96%, 97%, 98%, 99%, 99.5% or 99.9% homologous to the sequence of the heavy chain region described above. Preferably the heavy chain region is 97% homologous to the sequence of the heavy chain region described above.

This embodiment of the invention also extends to a light chain region with an amino acid sequence that is at least 80%, 85%, 90%, 95%, 96%, 97%, 98%, 99%, 99.5% or 99.9% homologous to the sequence of the light chain region described above. Preferably the light chain region is 97% homologous to the sequence of the light chain region described above.

In another embodiment, the present invention provides an antibody designated LD49, which comprises a heavy chain region comprising the following amino acid sequence:

(SEQ ID NO: 13)
DVQLVESGGG LVQPGGSRKL SCAASGFTFS NFGMHWVRQA

PEKGLEWVAY ISSGGSSINY ADTVKGRFTI SRDNPKNTLF

LQMTSLRSED TAIYYCTRGG TGTRSLYYFD YWGQGATLIV

SSDIPSTKGP SVFPLAPSSK STSGGTAALG CLVKDYFPEP

VTVSWNSGAL TSGVHTFPAV LQSSGLYSLS SVVTVPSSSL

GTQTYICNVN HKPSNTKVDK KVEPKSCDKT HTCPPCPAPE

LLGGPSVFLF PPKPKDTLMI SRTPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SRDELTKNQV SLTCLVKGFY PSDIAVEWES NGQPENNYKT

TPPVLDSDGS FFLYSKLTVD KSRWQQGNVF SCSVMHEALH

NHYTQKSLSL SPGK;

and a light chain region comprising the following amino acid sequence:

(SEQ ID NO: 14)
DIQMTQSPSS LSASVGDRVT ITCRASQDIG NFLNWYQQKP

GKAPKLLLYY TSRLQSGVPS RFSGSGSGTD YTLTISSLQP

EDFATYYCQQ GKTLPYTFGG GTKVEIKDIR TVAAPSVFIF

PPSDEQLKSG TASVVCLLNN FYPREAKVQW KVDNALQSGN

SQESVTEQDS KDSTYSLSST LTLSKADYEK HKVYACEVTH

QGLSSPVTKS FNRGEC

Still yet another embodiment of the invention is an antibody designated LD47, which comprises a heavy chain region comprising the following amino acid sequence:

(SEQ ID NO: 15)
QVQLVESGGG VVQPGRSLRL SCAASGFTFS NFGMHWVRQA

PGKGLEWVAY ISSGGSSINY ADTVKGRFTI SRDNSKNTLY

LQMNSLRAED TAVYYCTRGG TGTRSLYYFD YWGQGTTVTV

SSDIPSTKGP SVFPLAPSSK STSGGTAALG CLVKDYFPEP

VTVSWNSGAL TSGVHTFPAV LQSSGLYSLS SVVTVPSSSL

GTQTYICNVN HKPSNTKVDK KVEPKSCDKT HTCPPCPAPE

LLGGPSVFLF PPKPKDTLMI SRTPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SRDELTKNQV SLTCLVKGFY PSDIAVEWES NGQPENNYKT

TPPVLDSDGS FFLYSKLTVD KSRWQQGNVF SCSVMHEALH

NHYTQKSLSL SPGK;

and a light chain region comprising the following amino acid sequence:

(SEQ ID NO: 16)
DIQMTQSPSS LSASVGDRVT ITCRASQDIG NFLNWYQQKP

GKAPKLLIYY TSRLQSGVPS RFSGSGSGTD YTLTISSLQP

EDFATYYCQQ GKTLPYTFGG GTKVEIKDIR TVAAPSVFIF

PPSDEQLKSG TASVVCLLNN FYPREAKVQW KVDNALQSGN

SQESVTEQDS KDSTYSLSST LTLSKADYEK HKVYACEVTH

QGLSSPVTKS FNRGEC

A further embodiment of the invention is an antibody comprising a variant of the heavy chain variable region and/or heavy chain constant region as described above and a variant of the light chain variable region and/or light chain constant region as described above.

A variant of the heavy chain and light chain variable or constant regions of an antibody of the present invention is understood to mean the sequences of the heavy chain and light chain variable or constant regions with one or more deletions, insertions, or substitutions. Particular embodiments include, but are not limited to, heavy chain and light chain variable and constant regions described above that comprise from one to ten deletions, insertions or substitutions of amino acid residues, when compared to the heavy chain and light chain variable and constant regions described above. In one embodiment, a variant has an amino acid sequence that is at least 85% identical to the heavy chain and light chain variable regions described above and in another embodiment the variant has an amino acid sequence that is at least 90% identical to the heavy chain and light chain variable regions described above. The percent identity may be determined, for example, by comparing sequence information using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

A given amino acid may be replaced by any residue that does not adversely affect antibody function. The replacement residue can have similar physiochemical characteristics to the original residue i.e. a conservative substitution, although this is not essential. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

The percent identity of two amino acid sequences or of two nucleic acid sequences may be determined by aligning the sequences for optimal comparison purposes (e.g. gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those skilled in the art. The NBLAST and XBLAST programs are examples of computer programs which perform such algorithms. BLAST nucleotide searches can be performed with the NBLAST program to obtain nucleotide sequences homologous to nucleic acid molecules of the invention. BLAST protein searches can be performed with the XBLAST program to obtain amino acid sequences homologous to protein molecules of the invention.

To obtain gapped alignments for comparison purposes, Gapped BLAST can be utilized. Alternatively, PSI-Blast can be used to perform an iterated search which detects distant relationships between molecules (Idem.). When utilizing BLAST, Gapped BLAST, and PSI-Blast programs, the default parameters of the respective programs (e.g., XBLAST and NBLAST) can be used. Further suitable computer based algorithm programs can be utilized and will be known to the person skilled in the art.

The antibody described above or variants thereof can be modified post-translationally. Post-translational modification means the enzymatic processing of a polypeptide chain such as an antibody following its translation from its mRNA transcript. The post-translational modification may include the following activities:

(i) glycosylation which relates to the addition of carbohydrate moieties to the antibody molecule, (ii) phosphorylation which relates to the addition of a phosphate molecular group to the antibody molecule, (iii) sulfation which is the addition of sulfate molecular groups to the antibody, (iv) acetylation which is the addition of an acetyl molecular group to the antibody, (v) ribosylation which is the addition of a ribose molecular group to the aotibody, and (vi) cleavage which is the removal of a portion of the polypeptide chain and/or fragmentation of a single polypeptide into two or more fragments in order to produce a functional antibody in the correct environment.

Antibodies against tumor antigens can also be coupled to radioactive isotopes for therapeutic purposes, radioimmunotherapy. When infused into a patient, or delivered directly into a solid tumor or around a solid tumor, these radiation-carrying antibodies circulate in the body until they locate and bind to the surface of specific cells, and then deliver their cytotoxic radiation directly to the cancerous cells. Radioimmunotherapy has been already successfully employed for the treatment of several cancers, for example with the use of ZEVALIN, an Yttrium-90 labeled monoclonal antibody.

Currently, beta radiation emitting radionuclides are used almost exclusively in radioimmunotherapy. This is due to their relatively long path length in biological tissue (in the mm range), which is sufficient to irradiate cancer cells that do not have bound radiolabeled antibody. Beta-emitters provide a relatively uniform radiation dose to the tumour. However, the shorter-range alpha radiation emitters (50-100 mm) have been shown to be more efficient than beta-emitters at inducing lethal lesions in single cells. Therefore alpha emitters can also provide a favorable therapeutic index, for example in single tumour cells in the circulation, micrometastases and in certain cases, minimal residual disease. Therefore both alpha and beta emitter atoms can be coupled to the antibodies of the present invention to create a radioimmunotherapy.

In one embodiment of the present invention the antibodies of the present invention are labeled with any one of the following isotopes: Phosphorus-32 (beta), Scandium-47, Strontium-89 (beta), Yttrium-90 (beta), Rhodium-105 (beta and gamma), Tin-117m (gamma), Iodine-131 (beta and gamma), Samarium-153 (beta), Dysprosium-166 (beta and gamma), Erbium-169 (beta), Ytterbium-175 (beta), Lutetium-177, Rhenium-188 (beta), Osmium-194, Bismuth-212 (alpha), Bismuth-213 (alpha), Actinium-225 (alpha).

In another embodiment of the present invention the radiolabeled antibodies of the present invention are used for therapeutic purposes for the treatment of cancer.

There are many descriptions in the art on how to radiolabel antibodies for diagnostic or therapeutic purposes. Therefore it is considered to be well known in the art how to radiolabel an antibody and one would not be subjected to undue experimentation to create the radiolabeled antibodies of the present invention. For example, Fritzberg et al (Approaches to Radiolabeling of Antibodies for Diagnosis and Therapy of Cancer Pharmaceutical Research, Volume 5, Number 6/June, Pages 325-334, 1988) already describes methods for such labeling. U.S. Pat. No. 7,229,620 specifically describes methods to radiolabel an antibody with Yttrium-90. In "Direct radiolabeling of monoclonal antibodies with Rhenium-188 for radioimmunotherapy of solid tumors—a review of radiolabeling characteristics, quality control and in vitro stability studies" (Applied Radiation and Isotopes Volume 54, Issue 3, March 2001, Pages 399-406), it is described a method to radiolabel an antibody with Rhenium-188.

Methods for radiolabeling of antibodies can be grouped as follows: 1) the direct labeling in which the inner di-sulfide bonds (—S—S—) of the hinge-region of the antibodies are being partially reduced to sulfhydril groups (—SH). To do this, various chemical compounds having reducing properties are used, such as for example, the derivatives of ascorbic acid (Hnatowich D. et al. J. Nucl. Med. 1994; 35: 127-134), and/or substances with sulfhydryl groups or stannic-II-compounds or complexes (Mather S. et al. J. Nucl. Med. 1990; 31: 692-697, Rhodes B. J. Nucl. Med. 1986:27:685-693, and Thakur M. et al. Nucl. Med. Biol. 1991; 18: 227-233,) and 2) the indirect labeling methods in which mostly bi-functional complex forming agents are used, such as diamine-dithiol (Baidoo K. et al. Cancer Res. 1990:50:799-803), or a bi-functional ester of NHS-BAT (Eisenhut M. et al. J Nucl Med 1991; 37: 362-370), or diamid-dimercaptid (Kasina S. et al. J. Nucl. Med. 1991; 32: 1445-1451) and/or DTPA (Najafi A. et al. Int. J. Appl. Radiat. Isot. 1984; 5: 554-557), or a novel complex forming agent, which is based upon a N2S4-composition (Najafi A. et al. Nucl. Med. Biol. 1991; 18: 179-185, Qu T. et al. Radiochim. Acta 1993; 63: 209-212) for conjugating the radionuclide onto the antibodies. Other methods for indirect conjugation of the radionuclide to an antibody are based on the conjugation of thiol-groups to amino acids (e.g. lysine) in the protein molecule with 2-iminothiolan (Joiris E. et al. Nucl. Med. Biol. 1991, 18: 353-356) or with the groups of 1-imino-4-mercaptobutyl compounds (Goedemans W. in Nicolin M. et al. (eds.) Verona 1990; 595-603).

Suitable complex forming agents for the complex formation, especially with Yttrium (preferably Y-90) are, for example, DOTA (Denora et al. Anticancer Research 1997, 17, 1735-1744) or 12 N4-maleimid (tetra-azocyclododecantextra-acetic acid) (Turner et al. Br. J. Cancer, 1994, 70: 35-41, and King et al. Cancer Research, 1994, 54: 6176-6185). Particularly suited for complex formation of Rhenium (preferably Re-186 or Re-188), is for example, the MAG-3 complex forming agent (van Gog et al. J. Nucl. Med. 1996, 37, (2), 352-362). A chelator such as CHX-DTPA is disclosed in U.S. Pat. No. 5,641,471 for preparing and antibody with attached Bismuth-213. U.S. Pat. No. 5,246,691 discloses chelating agents to create antibodies with attached Actinium-225

Many isotopes like Phosphorus-32, Strontium-89, Yttrium-90, Samarium-153, Erbium-169, Ytterbium-175, Rhenium-188 have been stably coupled to antibodies for therapeutic purposes by means of bi-functional complex forming agents (while iodine has been known for many years to couple to antibodies, it is not particularly useful because of its unfavorable radiation properties).

Radiolabeled antibodies are important clinical reagents for both tumor imaging and therapy since they provide a direct mode of destruction by directing destructive radioactive energy to the cancer site via a homing antibody. For example, three radiolabeled antibodies—two murine, Y-90 ibritumomab tiuxetan (Zevalin; Biogen Idec) and 1-131 tositumomab (Bexxar; Corixa/GSK), and one chimeric, 1-131 ch-TNT (Shanghai Medipharm Biotech)—have been approved for non-Hodgkin's lymphoma or lung cancer.

It is an object of the present invention to use the radiolabeled antibody of the present invention as a therapy for cancer.

In another aspect, the present invention further extends to an antibody in combination with at least one different therapeutic or anti-melanoma drug. In one embodiment the therapeutic or anti-melanoma drug is a cytotoxic chemotherapy drug or combination of drugs such as dacarbazine, temozolomide, fotemustine, carmustine, lomustine, temozolomide, cisplatin, carboplatin, TAXOL, TAXOTERE, tamoxifen, vinblastin, vincristine, and DHFR inhibitors (e.g. piritrexim isethionate). Another embodiment is a drug to activate the immune system such as interleukin 2 (such as ALDESLEUKIN), interferon alpha and interferon alpha-2b, other cytokines/chemokines, or agents to activate lymphocytes such as IPILIMUMAB, TICILIMUMAB or other drugs designed to activate lymphocytes. In another embodiment, the drug is another monoclonal antibody that binds to melanoma, such as anti-GD2 antibodies or anti-HMW-MAA antibodies, antibodies that bind to tumor matrix, or antibodies designed to inhibit vascular structures such as BEVACICUMAB. Another embodiment is to add drugs that block critical biochemical pathways in melanoma, such as the MAPK pathway or the AKT/PI3K pathways. Examples of these drugs include, but are not limited to: SORAFENIB, AZD6244, PLX4032, XL281, PD0325901, SUNITINIB, and GLEEVEC.

The present invention also provides a method of treatment and/or prophylaxis of malignant melanoma, the method comprising the step of administering an antibody described above. The malignant melanoma can be advanced stage malignant melanoma, which is stage IV of the disease. Malignant melanoma is the most aggressive form of skin cancer. It is a malignant tumor of melanocytes, the cells which make melanin, the pigment that gives skin its colour and protects it from ultraviolet radiation. Malignant melanoma most commonly occurs in the skin but may also occur at any site to which melanocytes have migrated. Less frequently, the cancer may occur in the melanocytes of the retinal pigment epithelial cells (uveal melanoma). There are four main 'stages' of disease progression, Stages I to IV, with treatment becoming more problematic the more advanced the disease becomes.

The method of treatment of malignant melanoma with an antibody of the invention further comprises the step of treating a subject with other therapy used to treat melanoma such as radiation therapy or surgery. The other therapy such as radiation therapy can be administered simultaneous, separate or sequential to administration of an antibody of the invention to a subject.

The method of treatment can be in relation to a subject that has previously undergone surgery to treat the malignant melanoma. Alternatively, the method of treatment can be as a first line of treatment of malignant melanoma i.e. where the subject has not previously undergone surgery for treating the malignant melanoma.

This aspect of the invention includes treatment with an antibody described above in combination with at least one different therapeutic or anti-melanoma drug. The therapeutic or anti-melanoma drug may or may not be approved for treatment of malignant melanoma. In one embodiment the therapeutic or anti-melanoma drugs are those listed above. The antibody and the therapeutic or anti-melanoma drug can be administered simultaneously, separately or sequentially.

This aspect of the invention further extends to an antibody described above for treating malignant melanoma. This aspect also extends to the use of an antibody described above in the manufacture of a medicament for treating malignant melanoma.

This aspect of the invention also extends to a pharmaceutical composition comprising an antibody as described above. The composition or pharmaceutical composition may optionally further comprise a pharmaceutically-acceptable excipient, diluent or carrier.

Treatment/Therapy

The term "treatment" is used herein to refer to any regimen that can benefit a human or non-human animal. The treatment may be in respect of an existing condition or may be prophylactic (preventative treatment). Treatment may include curative, alleviation or prophylactic effects.

More specifically, reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Therapeutic" may also reduce the severity of an existing condition.

Administration

The antibody of the invention or variants may be administered to a patient in need of treatment via any suitable route. Route of administration may include; parenterally (including subcutaneous, intramuscular, intravenous, by means of, for example, a drip patch), some further suitable routes of administration include (but are not limited to) oral (including buccal and sublingual), rectal, nasal, topical, infusion, vaginal, intradermal, intraperitoneally, intracranially, intrathecal, intraocular or eyedrops, and epidural administration or administration via oral or nasal inhalation, by means of, for example a nebulizer or inhaler, or by an implant, or by isolated limb perfusion.

For administration via the oral or nasal inhalation routes the antibody may be delivered using a mechanical form including, but not restricted to, an inhaler or nebulizer device.

Further, where the oral or nasal inhalation routes are used, administration by a SPAG (small particulate aerosol generator) may be used.

For intravenous injection, the antibody composition ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, Lactated Ringer's injection. Preservatives, stabilizers, buffers, antioxidants and/or other additives may be included, as required.

Dose

The composition/antibody is preferably administered to an individual in a "therapeutically effective amount", this being sufficient to show benefit to the individual.

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

The optimal dose can be determined by physicians based on a number of parameters including, for example, age, sex, weight, severity of the condition being treated, the active ingredient being administered and the route of administration. Typical per patient doses of the antibody of the invention are between 3 mg and 1000 mg per metre squared per week.

In another aspect, the present invention relates to a method of producing the antibody described above comprising; i) the step of transfecting a host with a vector comprising a nucleic acid (NA) sequence that encodes the amino acid sequence of the antibody described above, ii) isolating the expressed antibody and iii) purifying the antibody. The nucleic acid can be DNA or RNA.

This aspect of the invention extends to the NA sequence encoding an antibody described above. This aspect of the invention also extends to a vector comprising the NA sequence encoding an antibody described above. This aspect of the invention further extends to a host cell transformed with the vector comprising the NA sequence encoding an antibody described above. This aspect of the invention further extends to a host cell that is an avian cell, such as a chicken, a plant cell or an animal cell Expression This aspect of the invention further provides recombinant cloning and expression vectors containing NA encoding an antibody described above, as well as host cells containing the recombinant vectors. Expression vectors comprising NA may be used to prepare an antibody, variant or fragment of the invention encoded by the NA. A method for producing antibodies, variants or fragments comprises culturing host cells transformed with a recombinant expression vector encoding the antibodies, variants or fragments described above, under conditions that promote expression of the antibodies, variants or fragments, then recovering the expressed antibodies, variants or fragments from the culture.

Any suitable expression system may be employed. The vectors include a NA encoding an antibody, variant or fragment of the invention, operably linked to suitable transcriptional or translational regulatory nucleotide sequences, such as those derived from a mammalian, avian, microbial, viral, bacterial, or insect gene. Nucleotide sequences are operably linked when the regulatory sequence functionally relates to the NA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A NA sequence for a signal peptide (secretory leader) may be fused in frame to the nucleic acid sequence of the invention so that the NA is initially transcribed, and the mRNA translated, into a fusion protein comprising the signal peptide. A signal peptide that is functional in the intended host cells promotes extracellular secretion of the antibodies, variants or fragments. The signal peptide is cleaved from the antibodies, variants or fragments during translation, but allows secretion of antibodies, variants or fragments from the cell.

Suitable host cells for expression of antibodies include higher eukaryotic cells, algae, and yeast. The higher eukaryotic cells can be avian cells and in particular chicken cells. This is described in WO2004/047531. In addition, the higher eukaryotic cells can be plant cells or animal cells. Mammalian cells, and in particular CHO cells are particularly preferred for use as host cells. Appropriate cloning and expression vectors for use with mammalian, prokaryotic, yeast, fungal and insect cellular hosts are described, for example, in Pouwels et at Cloning Vectors: A Laboratory Manual, Elsevier, N.Y., (1986) (ISBN 0444904018).

Established cell lines of mammalian origin also may be employed. Examples of suitable mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, murine NSO cells, HeLa cells, and BHK (ATCC CRL 10) cell lines, human Per.C6 cells, mouse SP2O cells and the CV1 IEBNA cell line derived from the African green monkey kidney cell line CV1 (ATCC CCL 70) as described by McMahan et al. (EMBO J. 10: 2821, 1991).

Established methods for introducing DNA into mammalian cells have been described (Kaufman, R. J., Large Scale Mammalian Cell Culture, 1990, pp. 15-69). Additional protocols using commercially available reagents, such as Lipofectamine or Lipofectamine 2000 lipid reagents (Gibco/BRL) or Lipofectamine-Plus lipid reagent, can be used to transfect cells (Felgner et al., Proc. Natl. Acad. Sci. USA 84:74137417, 1987). In addition, electroporation can be used to transfect mammalian cells using conventional procedures, such as those in Sambrook et al. (Molecular Cloning: A Laboratory Manual, 2 ed. Vol. 1-3, Cold Spring Harbor Laboratory Press, 1989). Selection of stable transformants can be performed using methods known in the art, such as, for example, resistance to cytotoxic drugs. Kaufman et al., Meth. in Enzymology 185:487-511, 1990, describes several selection schemes, such as dihydrofolate reductase (DHFR) to confer resistance to methotrexate. Other examples of selectable markers that can be incorporated into an expression vector include cDNAs conferring resistance to antibiotics, such as G418 (Geneticin) and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. NA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication.

Additional control sequences shown to improve expression of heterologous genes from mammalian expression vectors include such elements as the expression augmenting sequence element (EASE) derived from CHO cells (Monis et al., Animal Cell Technology, 1997, pp. 529-534 and PCT Application WO 97/25420).

Prokaryotic expression systems can be used for expression of antibodies, variants and fragments of the invention. Prokaryotic expression systems are particularly useful for the expression of fragments of antibodies of the invention. Prokaryotes include gram-negative or gram-positive organisms. Suitable prokaryotic host cells for transformation include, for example, *E. coli, Bacillus subtilis, Salmonella typhimurium*. In a prokaryotic host cell, such as *E. coli*, antibodies, variants or fragments may include an N-terminal methionine residue to facilitate expression of the recombinant in the prokaryotic host cell. The N-terminal methionine may be cleaved from the expressed recombinant antibodies, variants or fragments.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement Examples of useful expression vectors for prokaryotic host cells include those derived from commercially available plasmids such as the cloning vector pBR322 which contains genes for ampicillin and tetracycline resistance and thus provides simple means for identifying transformed cells. An appropriate promoter and a DNA sequence are inserted into the pBR322 vector.

The DNA which encodes the antibodies, variants or fragments of the invention may be cloned in-frame into the multiple cloning site of an ordinary bacterial expression vector. Typically the vector would contain an inducible promoter upstream of the cloning site, such that addition of an inducer leads to high-level production of the recombinant antibodies, variants or fragments when desired.

For expression of the recombinant antibodies, variants or fragments, the bacterial cells are propagated in growth medium until reaching a pre-determined optical density. Expression of the recombinant protein is then induced which activates expression of proteins from plasmids containing a lac operator/promoter. After induction (typically for 1-4 hours), the cells are harvested.

For recovery of the expressed antibodies, variants or fragments, the pelleted cells may be resuspended in ten volumes of 50 mM Tris-HCl (pH 8)/1 M NaCl and then passed two or three times through a French press. Most highly expressed recombinant antibodies, variants or fragments form insoluble aggregates known as inclusion bodies. Inclusion bodies can be purified away from the soluble proteins by pelleting in a centrifuge. The inclusion body pellet is washed and then dissolved in Tris-HCl. Any material that cannot be dissolved is removed by centrifugation.

The protein of interest (i.e. the antibodies, variants or fragments) will, in most cases, be the most abundant protein in the resulting clarified supernatant. This protein may be "refolded" into the active conformation. After refolding, purification can be carried out by a variety of chromatographic methods.

The antibodies, variants or fragments of the invention may be expressed in yeast host cells, preferably from the *Saccharomyces* genus (e.g., *S. cerevisiae*). Other genera of yeast, such as *Pichia* (*pichia pastoris*) or *Kluyveromyces*, may also be employed. Yeast vectors will often contain an origin of replication sequence from a 2 [mu] yeast plasmid, an autonomously replicating sequence (ARS), a promoter region, sequences for polyadenylation; sequences for transcription termination, and a selectable marker gene. Suitable promoter sequences for yeast vectors include, among others, promoters for metallothionine, 3-phosphoglycerate kinase (Hitzeman et al., J. Biol. Chem. 255:2073, 1980) or other glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase.

Leader sequences suitable for facilitating secretion of recombinant antibodies, variants or fragments from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., Proc. Natl. Acad. Sci. USA 75:1929, 1978.

Isolation and Purification

The invention also includes methods of isolating and purifying the antibody and fragments thereof. An isolated and purified antibody according to the invention can be produced by recombinant expression systems as described. Antibodies can be substantially purified, as indicated by a single protein band upon analysis by SDS-polyacrylamide gel electrophoresis (SDS-PAGE).

With respect to any type of host cell, as is known to the skilled artisan, procedures for purifying a recombinant antibody, variant or fragment will vary according to such factors as the type of host cells employed and whether or not the recombinant antibody, variant or fragment is secreted into the culture medium.

In general, the recombinant antibodies, variants or fragments can be isolated from the host cells if not secreted, or from the medium or supernatant if soluble and secreted, followed by one or more concentration, salting-out, ion exchange, hydrophobic interaction, affinity purification or size exclusion chromatography steps.

As to specific ways to accomplish these steps, the culture medium first can be concentrated using a commercially available protein concentration filter, for example, a Millipore Pellicon ultrafiltration unit. Following the concentration step, the concentrate can be applied to a purification matrix such as a gel filtration medium.

Alternatively, an anion exchange resin can be employed, for example, a matrix or substrate having pendant diethylaminoethyl (DEAB) groups. The matrices can be acrylamide, agarose, dextran, cellulose or other types commonly employed in protein purification. Alternatively, a cation exchange step can be employed. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the antibodies, variants or fragments can be employed. In one embodiment a proteinA affinity chromatography column is used. Other examples of such resins employed are lectin columns, dye columns, and metal-ehelating columns. Finally, one or more reversed-phase high performance liquid chromatography (RP-HPLC) steps employing apolar RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant antibodies, variants or fragments.

Transformed yeast host cells are preferably employed to express antibodies, variants or fragments as a secreted polypeptide in order to simplify purification. Secreted recombinant antibodies, variants or fragments from a yeast host cell fermentation can be purified by methods which are well known to those skilled in the art.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

The invention being generally described, will be more readily understood by reference to the following examples which are included merely for purposes of illustration of certain aspects and embodiments of the present invention, and are not intended to limit the invention.

EXAMPLE 1

Production of CDR-grafted Humanized R24 Antibodies

The hybridoma cell line R24, created from mice immunised with human melanoma cells (see Dippold, W. G. et al., Proc. Natl. Acad. Sci. USA (1980) 77 (10):6114-6118) secretes an IgG3 antibody which is specific for the ganglioside GD3. The ganglioside GD3 is a tumour associated antigen overexpressed on most human melanomas.

The gene sequence for the R24 antibody has been submitted to the NCBI database: the kappa chain variable domain accession number is GI:6573606 and the gamma chain variable domain accession number is GI:6573607 (Kaminski, M. J. et al. J. Biol. Chem. (1999) 274 (9):5597-5604).

On analysis, the R24 kappa (vk) chain variable domain belongs to mouse subgroup 5 which corresponds to human subgroup 1 for the purpose of CDR grafting. The canonical class of each CDR was identified: CDR-L1 belongs to canonical class 2 (form B) (Al-Lazikani, B., Lesk, A. M., Chothia, C. J., Mol. Biol. (1997) 273:927-948), and both CDR-L2 and CDR-L3 belong to canonical class 1. The non-redundant database from NCBI was searched for suitable human frameworks into which to graft the murine CDRs. The vk design was based on a human vk sequence with accession number GI: 2597947 (Juul, L., Houghs, L., Barington, T., Immunogenetics (1998) 48 (1):40-46). This belongs to human subgroup 1 and germline VkLa.

The R24 heavy (vh) chain variable domain was identified as belonging to mouse miscellaneous subgroup 3. CDR-H1 belongs to canonical class 1, and CDR-H2 belongs to canonical class 3. The CDR-H3 does not fall into any canonical class, but is likely to form a kinked base according to the rules of Shirai (Shirai, H., Kidera, A., Nakamura, H., FEBS Letters (1999) 455:188-197). The non-redundant database from NCBI was searched for suitable human frameworks into which to graft the murine CDRs. The vh design was based on a human vh sequence with accession number 01: 106423 (Shroeder, H. W and Wang, J. Y., Proc. Natl. Acad. Sci. USA (1990) 87:6146-6150). This sequence belongs to human subgroup 3 and germline vh3-30.

The structure of the vk and vh sequences of R24 are available in the Protein Data Bank with codes IBZ7 and IR24, respectively (Kaminski, M. J. et al., J. Biol. Chem. (1999) 274 (9):5597-5604). These structures were used to guide the choice of back mutations likely to give a better fit for the grafted CDRs.

The CDR-grafted vk design for LD47:

```
                                              (SEQ ID NO: 17)
DIQMTQSPSSLSASVGDRVTITCRASQDIGNFLNWYQQKPGKAPKLLIYYTSRLQSGVPSRF

SGSGSGTDYTLTISSLQPEDFATYYCQQGKTLPYTFGGGTKVEIK.
```

In this sequence leucine 48 is back mutated to isoleucine as isoleucine is a canonical residue for CDR-L2.

The CDR-grafted vk design for LD49 is a straight CDR-graft with no back mutations:

```
                                              (SEQ ID NO: 18)
DIQMTQSPSSLSASVGDRVTITCRASQDIGNFLNWYQQKPGKAPKLLLYY

TSRLQSGVPSRFSGSGSGTDYTLTISSLQPEDFATYYCQQGKTLPYTFGG

GTKVEIK.
```

The CDR-grafted vh design for LD47:

```
                                              (SEQ ID NO: 19)
QVQLVESGGGVVQPGRSLRLSCAASGFTFSNFGMHWVRQAPGKGLEWVAY

ISSGGSSINYADTVKGRFTISRDNSKNTLYLQMNSLRAEDTAVYYCTRGG

TGTRSLYYFDYWGQGTTVTVSS.
```

In this sequence alanine 93 is back mutated to threonine as this residue contacts several residues in CDR-H3.

The heavy chain variable region in LD49 is that of the original murine antibody, no CDR grafting was involved, i.e., the LD49 gamma chain is a chimeric mouse-human antibody chain.

Other back mutations were made and tested, however these were not found to have any beneficial effect to the antibodies' affinity or effector functions.

The sequences for the human IgG1 and kappa constant regions were obtained from the NCBI database accession numbers GI:49522738 and GI:62531193 respectively (Strausberg, R. L. et al., Proc. Acad. Sci. USA (2002) 99 (26):16899-16903).

The LD47 antibody was made up of the following heavy (gamma) and light (kappa) variable domain chains:

Chimeric Gamma:
(SEQ ID NO: 20)
DVQLVES GGGLVQPGGS RKLSCAASGF TFSNFGMHWV

RQAPEKGLEW VAYISSGGSS INYADTVKGR FTISRDNPKN

TLFLQMTSLR SEDTAIYYCT RGGTGTRSLYYFDYWGQGATLIVSS.

CDR grafted Kappa 1 back mutation:
(SEQ ID NO: 21)
DIQMTQSPSSLSASVGDRVTITCRASQDIGNFLNWYQQKPGKAPKLLIYY

TSRLQSGVPSRFSGSGSGTDYTLTISSLQPEDFATYYCQQGKTLPYTFGG

GTKVEIK.

The LD49 antibody was made up of the following heavy (gamma) and light (kappa) variable domain chains:

CDR grafted gamma one back mutation:
(SEQ ID NO: 22)
QVQLVESGGGVVQPGRSLRLSCAASGFTFSNFGMHWVRQAPGKGLEWVAY

ISSGGSSINYADTVKGRFTISRDNSKNTLYLQMNSLRAEDTAVYYCTRGG

TGTRSLYYFDYWGQGITVTVSS.

CDR grafted Kappa, no back mutations:
(SEQ ID NO: 23)
DIQMTQSPSSLSASVGDRVTITCRASQDIGNFLNWYQQKPGKAPKLLLYY

TSRLQSGVPSRFSGSGSGTDYTLTISSLQPEDFATYYCQQGKTLPYTFGG

GTKVEIK.

The Glutamine Synthetase Gene Expression System uses the GS gene as a selectable marker to facilitate the high level expression of recombinant proteins. This allows the rapid generation of high-yielding stably-transfected cell lines expressing recombinant antibodies. Double-gene plasmid constructs have been engineered for the LD47 and LD49 sequences above. Chinese Hamster Ovary (CHO) cells were transfected by electroporation, and the resultant antibody-expressing clones were expanded.

For each recombinant antibody, 2 litres of culture material was obtained. Purification of antibody from this material was achieved by protein A affinity chromatography. The recovered antibodies were then buffer exchanged into PBS, pH 7.0. The concentrations of all buffer exchanged antibodies were recalculated by ELISA and optical density readings at 280 nm and 260 nm (using Beer-Lambert's Law A=$\epsilon$.c.l; $\epsilon$=1.4 mL·mg$^{-1}$·cm$^{-1}$ for antibodies) and ranged from 0.56-1.29 mg/ml for ELISA results and 0.53-1.08 mg/mL for 280 nm results, Table 1. Although a discrepancy exists between ELISA and 280 nm concentration values the difference between each result is relative see Table 1.

TABLE 1

Concentrations Of Buffer Exchanged Antibodies As Measured By ELISA And Optical Density

| Antibody Name | Gamma Chain | Kappa Chain | ELISA concentration mg/ml | A280 concentration mg/ml |
|---|---|---|---|---|
| LD47 | CDR grafted 1 back mutation | CDR-grafted 1 back mutation | 0.85 | 0.7 |
| LD49 | Chimeric gamma | CDR-grafted no back mutation | 1.001 | 1.07 |

EXAMPLE 2

Immunofluorescence Assay

Initial studies looked at binding of the humanized antibodies to human melanoma SK-MEL28 cells which express GD3. Binding of antibodies to target cells was assayed by direct immunofluorescence using a FITC-labeled secondary antibody. Samples were analysed by one colour cytofluorimetric analysis.

Both LD47 and LD49 showed a high binding affinity to SK-MEL 28 cells. In order to overcome problems in one of the effector function assays a different GD3 expressing cell line was obtained, the human melanoma cell line MeWo. Several binding assays were repeated using this cell line the results are shown in FIG. 1.

Antibodies were tested in separate experiments that gave different MLF responses of the reference R24 antibody. To enable comparison between the different tested antibodies, 30% of maximum binding of R24 was calculated for each antibody. A figure of 30% was chosen for comparison as some of the antibodies tested (not shown here) bound at low levels in the concentration range tested and did not produce a higher relative MLF. Especially as the antibodies show homophilic binding and do not saturate the ganglioside GD3 antigen, the comparison gives a numerical indication of the relative abilities of the tested antibodies to bind ganglioside GD3. The results are shown in Table 2.

TABLE 2

Binding And Cytotoxicity Assays

| Antibody Name | Binding (30% of maximum) (ug/ml) | % cytotoxicity at 10 ug/ml |
|---|---|---|
| LD47 | 12.4 | 59.18 |
| LD49 | 30.8 | 57.8 |

Figure 2:
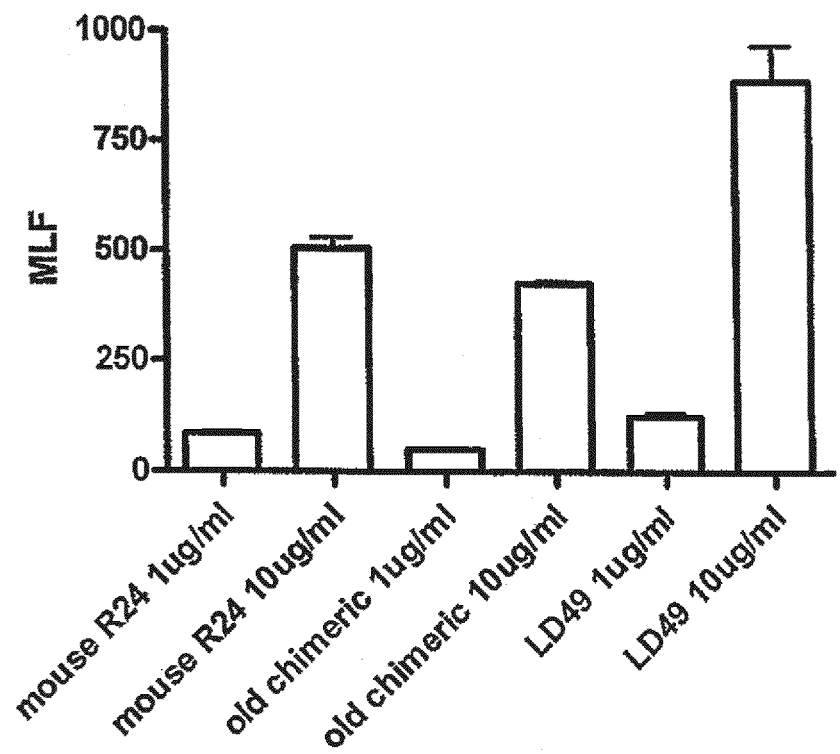
FIG. 2 illustrates the binding of the LD49 antibody, the murine R24 antibody and a previously published chimeric antibody to the SK-MEL28 cells.

An experiment using immunofluorescence was also performed to compare the binding of the LD49 antibody of the invention to SK-MEL28 cells with the binding of the murine R24 antibody and a chimeric antibody published in Chapman et al., in Cancer Immunol. Immunother. (1994) 39: 198-204. The LD49 antibody performed significantly better than the chimeric antibody as illustrated by FIG. 2.

Biacore Assay

Figure 3:
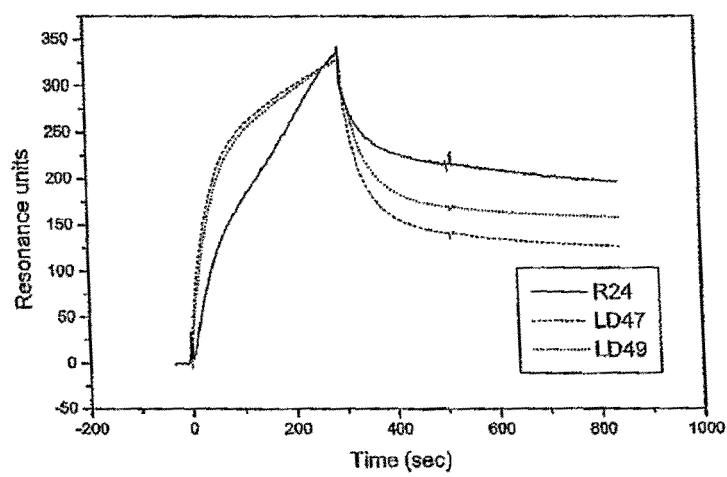
FIG. 3 illustrates Biosensor analysis of the interaction between humanized antibodies LD41-LD52 and immobilized GD3. The 'Off' rates were normalized to give identical 'injection end point' RU values.

Analyses were performed using a BIACORE 1000 biosensor system equipped with a carboxymethyldextran-coated CM5 chip according to Catimel (Catimel et al., 25 Glycobiology (1998) 8 (9): 927-938). Ganglioside GD3 (1 mg/ml in methanol) was diluted 1:4 with HEPES buffer and injected over the biosensor chip in order to immobilize the ganglioside. The antibodies were then diluted to the required concentrations with HEPES buffer and injected over the immobilized GD3. Biosensor curves were obtained as shown in FIG. 3 for LD41, LD49 and the murine R24 antibody.

LD47 and LD49 bind to the GD3 with similar affinity as the murine R24 antibody and not only do they display rapid association to the GD3, they also display slow dissociation.

GD3 ELISA

Figure 4:
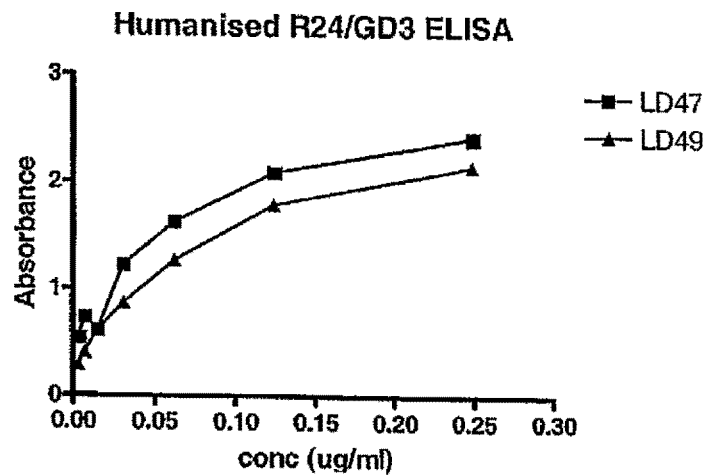
FIG. 4 illustrates binding of LD47 and LD49 humanized R24 antibodies to human ganglioside GD3.

An ELISA to measure antibody binding to ganglioside GD3 was performed to confirm that the antibodies were indeed binding to the ganglioside GD3. Plates were coated with human disialoganglioside GD3 and antibodies added to the plate over a range of concentrations. The antibodies appeared to display varying degrees of binding to GD3 as was the case with the binding assay and comparable results were obtained on each occasion the ELISA was performed. FIG. 4 illustrates one set of results obtained. These results correlate with the results from the binding assay.

EXAMPLE 3

Figure 5:
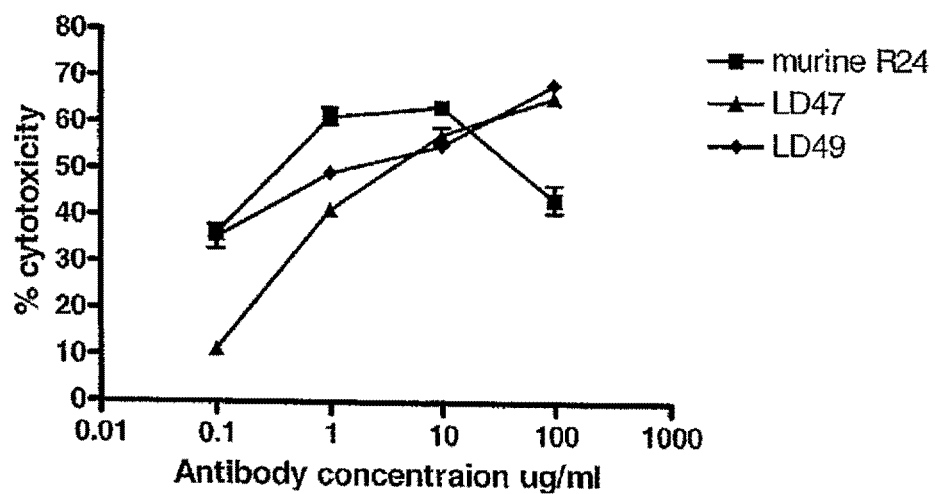
FIG. 5 illustrates lysis of MeWo cells by complement. The experiment was performed in triplicate and the results are presented as mean % cytotoxicity+/−standard error.

The humanized antibodies were assessed to determine their ability to mediate CDC. The ability of the humanized antibodies to fix human complement was examined using MeWo cells. In the complement assay, antibody diluted in medium was added to the MeWo cells. Human serum complement was also added to final concentration of 5% and the cells incubated for 2 hours at 37° C. Subsequently, dead cells stained with propidium iodide were identified by flow cytometry. Antibody concentrations from 100 ug/ml to 0.1 ug/ml were used. The results are shown in FIG. 5. In order to compare the humanized antibodies the % cytotoxicity at 10 ug/ml was calculated and is shown in Table 2.

EXAMPLE 4

Figure 6:
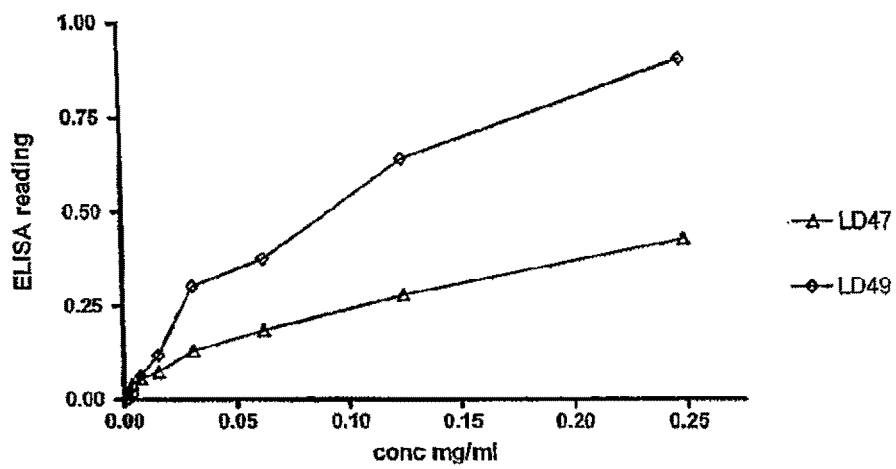
FIG. 6 illustrates homophilic binding of humanized R24 antibodies to mouse R24.

In order to determine the homophilic properties of the humanized antibodies their ability to bind to mouse R24 was measured. An ELISA plate was coated with the murine R24 and antibody binding was measured over a range of concentrations. FIG. 6 shows the results of the homophilic binding ELISA.

The results illustrate that LD47 and LD49 exhibit good homophilic binding. This was repeated on three occasions and the results were comparable.

EXAMPLE 5

Figure 7:
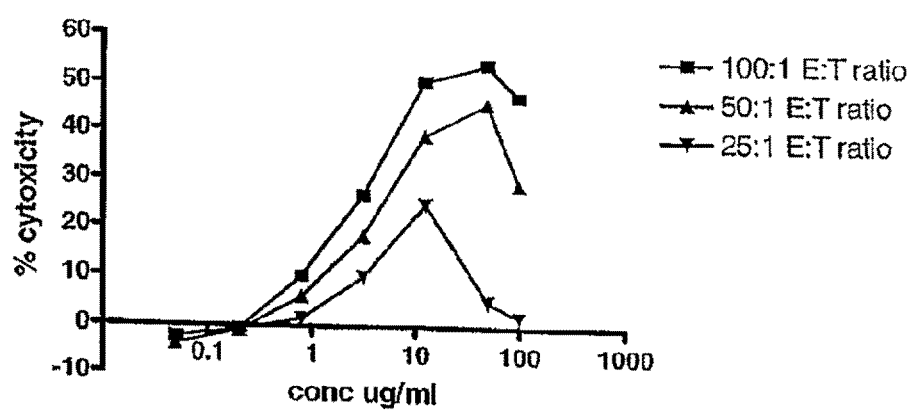
FIG. 7 illustrates the effect of antibody concentration and E:T ratio on LD49's ability to mediate ADCC.

ADCC was measured by the ability of the effector lymphocytes and monocytes to lyse target cells. Histopaque-separated PBMCs (obtained from buffy coats) were incubated with CFSE (carboxyfluoroscein succinimidyl ester)-stained MeWo cells and antibody. Subsequently, the dead cells were stained with propidium iodide and two colour cytofluorimetric analysis was performed. Initially, in order to determine the ideal concentration of antibody and effector to target (E:T) ratio LD49 was assayed at 0.05-100 ug/ml and 100:1, 50:1 and 25:1 effector to target ratios. FIG. 7 shows the results of this experiment. Above 12.5 ug/ml the antibodies' ability to mediate ADCC appears to decrease.

Figure 8:
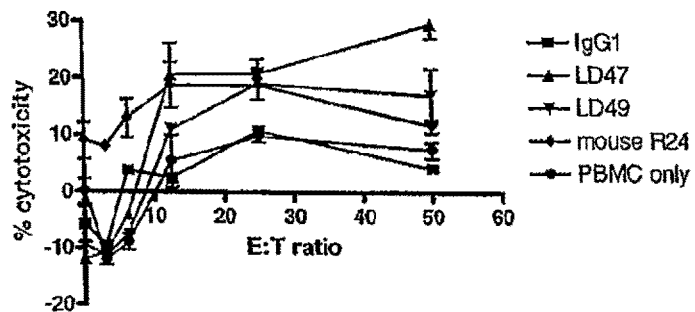
FIG. 8 illustrates ADCC over a range of E:T ratios. The experiment was performed in triplicate and the results are presented as mean % cytotoxicity+/standard error.

In order to compare the ability of the antibodies to mediate ADCC an ideal E:T ratio and antibody concentration has to be determined. For this, the lead antibodies LD47 and LD49 were tested for their ability to mediate ADCC over a range of effector: target cell (E:T) ratios and antibody concentrations (See FIG. 8). From this an ideal E:T ratio of 25:1 was chosen for all subsequent experiments.

Figure 9:
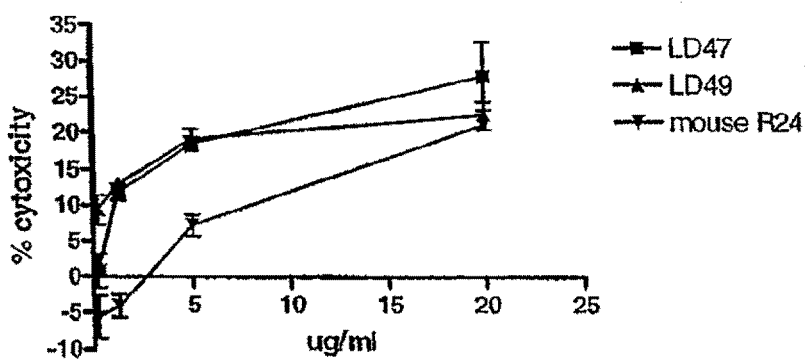
FIG. 9 illustrates ADCC over a range of antibody concentrations. The experiment was performed in triplicate and the results are presented as mean % cytotoxicity+/−standard error.

The effect of R24, LD47 and LD49 at a range of antibody concentrations was then investigated (FIG. 9). LD47 and LD49 showed high levels of ADCC mediation that were similar to the R24 murine antibody. PBMC-only and the IgG1 isotype control both gave negative cytotoxicity values and are not shown on the graph. The % cytotoxicity results in this experiment were low, possibly due to the variation between buffy coats. In this experiment, the ability of the antibodies to mediate ADCC did not decrease above 12.5 ug/ml as seen in FIG. 7.

Figure 10:
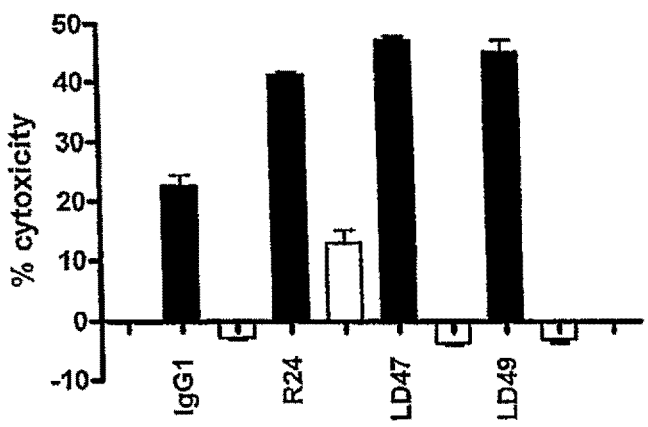
FIG. 10 illustrates repeated ADCC experiments with (shaded) and without (white) PBMC for humanized LD47 and LD49 R24 antibodies. The experiment was performed in triplicate and the results are presented as mean % cytotoxicity+/−standard error.

This experiment was repeated on three occasions. FIG. 10 shows the results for both with and without PBMCs and the LD47 and LD49 repeatedly demonstrated efficient ADCC, which was superior to the murine R24 antibody. In each experiment an E:T ratio of 25:1 was used and the antibodies were at a concentration of 10 ug/ml.

EXAMPLE 6

Phase I Studies of Humanized R24 Antibodies

The following studies are designed to determine the toxicity, pharmacokinetics, tumor targeting, and immunogenicity of humanized R24 antibodies. One goal is to select a phase II dose and schedule.

To be eligible for this trial, patients will be required to meet the usual eligibility criteria.

Major Eligibility Criteria

1. Patients with stage III or IV melanoma not curable by surgery.
2. ECOG performance status ≥2. Life expectancy >3 months.
3. Prior therapy for melanoma will be allowed but all prior melanoma therapy must have been completed at least 2 weeks prior to starting humanized R24 and all toxicities of prior therapy must have resolved.
4. Patients must have adequate organ and marrow function.

Major Exclusion Criteria

1. Prior treatment with a monoclonal antibody.
2. Concurrent immunosuppressive therapy (including steroids) or patients who are likely to require steroids or immunosuppressive therapy in the near future.
3. Patients with brain metastases will be excluded because of concern about humanized R24 causing serious hypertension.
4. Since hypertension may be a DLT, patients with poorly-controlled hypertension are excluded.
5. Because of concern about of GD3 in the developing CNS, children under 18 years of age, pregnant women, and women breast-feeding are excluded.

Treatment Plan

A cycle of treatment will consist of 4 weekly IV infusions of humanized R24. Up to two additional treatment cycles can be administered after a rest period of 2-4 weeks if toxicity is acceptable and there is no progression of disease.

Dose levels: Three patients will be accrued into the following escalating dose levels: 1, 5, 25, 125 mg/m$^2$. These dose levels were chosen based on the experience with mouse R24.

If DLT is observed in 1 patient, the cohort will be expanded to 6 patients. If DLT is observed in 2 or more patients at a dose level, that dose level will be considered to be above the DLT. In this case, a cohort of 3 patients will be accrued at a dose level intermediate between the toxic dose level and the prior dose level. If that intermediate dose level proves to be tolerated (i.e. ≥1 DLT), a final cohort can be accrued in a higher intermediate dose. On the other hand, if the first intermediate dose is not tolerable, then a final cohort can be accrued in to a lower intermediate dose. Up to 6 patients may be accrued into the cohort thought to represent the MTD in order to confirm safety.

Serum for pharmacokinetics will be collected pre-treatment and 1 hr, 2 hrs, 4 hrs, 2 days, 4 days, and 7 days after the first treatment of each treatment cycle. Serum R24 levels can be measured by ELISA using BEC2 murine anti-idiotypic MAb. Serum can also be assayed for human anti-human R24 antibody responses (HAHA). For this ELISA, F(ab')$_2$ fragments of humanized R24 will be prepared and used to coat 96-well plates (1 μg/well). Bound human IgG can be detected using an alkaline phosphatase-conjugated second antibody specific for human Fc.

EXAMPLE 7

Phase II Studies of Humanized R24 Antibodies

The following studies are designed to test huR24 alone and in combination with other therapeutic agents. A goal is to select a regimen worthy of further testing in a randomized trial design.

The eligibility and exclusion criteria for these phase II trials will be typical for phase II trials (and similar to the criteria indicated above for the phase I trial) although prior non-cytotoxic therapy (e.g. IL-2, signal transduction inhibitors) would be allowed.

One phase II trial would certainly explore treatment with MAb alone. However, experience with other MAbs (e.g. rituximab, cetuximab, trastuzimab, bevacizumab) indicates that humanized R24 may be more effective in combination with an active chemotherapy regimen. Therefore, parallel phase II trials can be done to combine humanized R24 with either temozolomide (TMZ) or a more active combination chemotherapy regimen such as CVD.

Other attractive agents to combine with huR24 would include, but are not limited to:

|  | Pre | Day 0 | Day 2 | Day 4 | Wk 2 | Wk 3 | Wk 4 | Wk 5 | Wk 6 |
|---|---|---|---|---|---|---|---|---|---|
| Humanized R24 treatment |  | X |  |  | X | X | X |  |  |
| Physical exam | $X_a$ |  |  |  | X |  | X |  | X |
| CBC, comp | $X_a$ |  |  |  | X | X | X |  | X |
| LDH | $X_a$ |  |  |  |  |  |  |  | X |
| CT, chest/abd/pelvis | $X_b$ |  |  |  |  |  |  | $X_e$ |  |
| EKG | $X_b$ |  |  |  |  |  |  |  |  |
| Brain MRI | $X_b$ |  |  |  |  |  |  |  |  |
| Urine catecholamines |  | $X_c$ |  |  |  |  |  |  |  |
| Pharmacokinetics |  | $X_d$ | X | X | X |  |  |  |  |
| Anti-humanized R24 Ab |  | X |  |  |  |  |  |  | X |
| $_{111}$In-Imaging |  | X | X | X |  |  |  |  |  |

$^a$Within 2 weeks of starting treatment.
$^b$Within 4 weeks of starting treatment.
$^c$Collected after treatment prior to being discharged home.
$^d$Pretreatment, 30 min, 1 hr, 2 hrs, and 4 hrs after completing the infusion.
$^e$CT scan can be done any time during weeks 5 or 6.

Tumor Targeting Studies

A critical parameter to measure is how much MAb reaches the tumor. Patients will receive 6-8 mCi of In-111 chelated by 5 mg of DOTA-hu-R24 per infusion. DOTA (1,4,7,10-tetraazacyclododecane-N,N',N'',N'''-tetraacetic acid) can be conjugated to hu-R24 by random coupling of one of the four available carboxylic acids of DOTA to a terminal amine on the antibody. The manufacture of this conjugate can be performed under cGMP conditions and the material analyzed for sterility, pyrogen content, immunoreactivity, number of DOTAs attached per antibody, chelate stability, animal biodistribution and acute toxicity.

Three patients in each cohort of the phase I trial will be imaged. Planar and/or SPECT images can be obtained 2-4 hours, 2-3 days and 4-6 days after the end of infusion of radiolabeled HuR24. Blood samples for PK analysis can be collected at predose, 30 min, 60 min, 2 h, 4 h, 24 h, approximately 48 to 72 hours (2-3 days) and 96-144 hours (4-6 days) after each infusion of radiolabeled antibody. Samples will be analyzed using RIA for concentrations of HuR24. Serum clearance will also be measured measuring $^{111}$In.

β Glucan: This sugar has been shown to enhance complement-mediated cytotoxicity. It would be of interest to see if β glucan enhances the antitumor effects of huR24.

Ipilimumab: This anti-CTLA4 MAb activates T cells and has anti-melanoma activity on its own. The drawback is that the T cell activation is non-specific. By co-administering huR24, it may be possible to focus the induced immune reactivity on GD3+ cells.

Biostatistics

Each of these phase II trials can be designed to use a Simon minimax two stage design in which a 10% response rate is considered not promising, a 30% response rate is considered promising, and the probabilities of a type I error and type II error are set at 0.10. In the first stage of this design, 16 patients will be accrued to each cohort. If at least 2 patients achieve a response among these 16 patients, then an additional 9 patients will be accrued to the second stage. If ≤4 responses are seen, the study will be terminated and declared negative. This design yields at least a 0.90 probability of a positive result if the true response rate is at least 30% and yields a 0.90 probability of a negative result if the true response rate is 10%.

What is claimed is:

1. An antibody comprising a heavy chain variable region that has the sequence of SEQ ID NO:25, and a light chain variable region that has the sequence of SEQ ID NO:4, wherein said antibody specifically binds to GD3.

2. The antibody of claim 1, wherein the antibody is radio-labeled.

3. A composition comprising the antibody of claim 1.

4. The composition of claim 3, further comprising a therapeutic or an anti-melanoma drug.

5. The composition of claim 4, wherein the therapeutic or anti-melanoma drug is selected from the group consisting of one or more cytotoxic drugs, interleukins, drugs that activate the immune system or lymphocytes, antibodies that bind to melanoma, antibodies that bind to tumor matrix, antibodies designed to inhibit vascular structures, and drugs that block critical biochemical pathways in melanoma.

* * * * *